US011992818B2

(12) United States Patent
Hartman et al.

(10) Patent No.: US 11,992,818 B2
(45) Date of Patent: May 28, 2024

(54) METHOD AND APPARATUS FOR THE RAPID DISCOVERY AND DESIGN OF POLYMERIZATIONS

(71) Applicant: NEW YORK UNIVERSITY, New York, NY (US)

(72) Inventors: Ryan Lee Hartman, New York, NY (US); Benjamin A. Rizkin, Brooklyn, NY (US)

(73) Assignee: New York University, New York, NY (US)

( * ) Notice: Subject to any disclaimer, the term of this patent is extended or adjusted under 35 U.S.C. 154(b) by 858 days.

(21) Appl. No.: 16/999,842

(22) Filed: Aug. 21, 2020

(65) Prior Publication Data

US 2021/0060514 A1 Mar. 4, 2021

Related U.S. Application Data

(60) Provisional application No. 62/892,453, filed on Aug. 27, 2019.

(51) Int. Cl.
| | | |
|---|---|---|
| *G16C 60/00* | (2019.01) | |
| *B01J 19/00* | (2006.01) | |
| *C08F 4/6592* | (2006.01) | |
| *G16C 20/10* | (2019.01) | |
| *G16C 20/70* | (2019.01) | |

(52) U.S. Cl.
CPC ....... *B01J 19/0033* (2013.01); *B01J 19/0013* (2013.01); *C08F 4/65925* (2013.01); *C08F 4/65927* (2013.01); *G16C 20/10* (2019.02); *G16C 20/70* (2019.02); *G16C 60/00* (2019.02); *B01J 2219/00058* (2013.01); *B01J 2219/00069* (2013.01); *B01J 2219/00072* (2013.01);

(Continued)

(58) Field of Classification Search
CPC ............... B01J 19/0033; B01J 19/0013; B01J 2219/00058; B01J 2219/00069; B01J 2219/00072; B01J 2219/00164; C08F 4/65925; C08F 4/65927; G16C 20/10; G16C 20/70; G16C 60/00
See application file for complete search history.

(56) References Cited

U.S. PATENT DOCUMENTS

| | | | | |
|---|---|---|---|---|
| 6,106,785 A | * | 8/2000 | Havlena .................. | C08F 10/00 422/62 |
| 2008/0097637 A1 | * | 4/2008 | Nguyen ............. | G05B 23/0254 700/110 |

OTHER PUBLICATIONS

Ahmadi, et al., "New Approach in Modeling of Metallocene-Catalyzed Olefin Polymerization Using Artificial Neural Networks," Macromolecular Theory and Simulations 18(3), pp. 195-200 (2009).

(Continued)

*Primary Examiner* — Manuel A Rivera Vargas
(74) *Attorney, Agent, or Firm* — Foley & Lardner LLP

(57) ABSTRACT

A reactor system includes at least one reactant provided to perform a reaction. The system includes one or more sensors configured to detect sensor data regarding the reaction. The system includes processing circuitry configured to receive the sensor data from the one or more sensors, apply one or more machine learning models to the sensor data to generate a measurement regarding at least one of the reaction or an activity of at least one catalyst used to perform the reaction, and control at least one of a temperature of the reactor, a flow rate of the at least one reactant, or a concentration of the at least one reactant responsive to the measurement.

20 Claims, 17 Drawing Sheets

(52) U.S. Cl.
CPC ............... *B01J 2219/00164* (2013.01); *B01J 2219/00195* (2013.01)

(56) References Cited

OTHER PUBLICATIONS

Bochmann, et al., "Synthesis of Base-Free Cationic Zirconium Methyl and Benzyl Complexes. The Crystal and Molecular Structure of {C5H3(SiMe3)2-1,3}2ZrMe(.mu.-Me)B(C6F5)3," Organometallics 13(6), pp. 2235-2243 (1994).
Chan & Nascimento, "Use of neural networks for modeling of olefin polymerization in high pressure tubular reactors," Applied Polymer Science 53(10), pp. 1277-1289 (1994).
Charoenpanich, et al., "Estimation of Polymerization Conditions Needed to Make Ethylene/1-olefin Copolymers with Specific Microstructures Using Artificial Neural Networks," Macromolecular Reaction Engineering 10(3), pp. 215-232 (2016).
Chen & Marks, "Cocatalysts for Metal-Catalyzed Olefin Polymerization:? Activators, Activation Processes, and Structure-Activity Relationships," Chemical Reviews 100(4), pp. 1391-1434 (2000).
Chetouani, "Using Artificial Neural networks for the modelling of a distillation column," International Journal of Computer Science & Applications 4(3), pp. 119-133 (2007).
Christianson, et al., "Stopped-Flow NMR: Determining the Kinetics of [rac—(C2H4(1-indenyl)2)ZrMe][MeB(C6F5)3]-Catalyzed Polymerization of 1-Hexene by Direct Observation," Journal of the American Chemical Society 132(33), pp. 11461-11463 (2010).
Christopher, et al., "Synthesis, Structure, and Reactivity of rac—Me2Si(indenyl)2Zr(NMe2)2," Organometallics 15(19), pp. 4038-4044 (1996).
Cruz, et al., "3D-QSAR analysis of metallocene-based catalysts used in ethylene polymerization," Polymer 45(6), pp. 2061-2072 (2004).
Cruz, et al., "3D-QSAR as a Tool for Understanding and Improving Single-Site Polymerization Catalysts. A Review," Organometallics 33(12), pp. 2944-2959 (2014).
Cruz, et al., "3D-QSAR study of ansa-metallocene catalytic behavior in ethylene polymerization," Polymer 48(16), pp. 4663-4674 (2007).
Cruz, et al., "QSAR model for ethylene polymerisation catalysed by supported bis(imino)pyridine iron complexes," Polymer 48(26), pp. 7672-7678 (2007).
Cruz, et al., "Structure-Activity Relationship Study of the Metallocene Catalyst Activity in Ethylene Polymerization," Organometallics 24(21), pp. 5095-5102 (2005).
Curteanu & Leon, "Optimization strategy based on genetic algorithms and neural networks applied to a polymerization process," Quantum Chemistry 108(4), pp. 617-630 (2008).
Curteanu, et al., "Artificial intelligence modelling methodologies applied to a polymerization process," 4th International Conference On Simulation And Modeling Methodologies, Technologies And Applications, pp. 43-49 (2014).
D'agnillo, et al., "Effect of operating conditions on the molecular weight distribution of polyethylene synthesized by soluble metallocene/methylaluminoxane catalysts," Macromolecular Chemistry and Physics 199(6), pp. 955-962 (1998).
Dare, et al., "Polymerization of propene with tBuNSiMe2C5Me4TiMe2: Effects of trialkylaluminiums as additives," Bulletin of the Chemical Society of Ethiopia 18(2), pp. 131-141 (2004).
Drummond & Sumpter, "Use of Drug Discovery Tools in Rational Organometallic Catalyst Design," Inorganic Chemistry 46(21), pp. 8613-8624 (2007).
Ewen, "Mechanisms of stereochemical control in propylene polymerizations with soluble Group 4B metallocene/methylalumoxane catalysts," Journal of the American Chemical Society 106(21), pp. 6355-6364 (1984).
Fazilat, et al., "Predicting thermal degradation kinetics of nylon6/feather keratin blends using artificial intelligence techniques," Polymer 53(11), pp. 2255-2264 (2012).

Filho & Filho, "Hybrid training approach for artificial neural networks using genetic algorithms for rate of reaction estimation: Application to industrial methanol oxidation to formaldehyde on silver catalyst," Chemical Engineering Journal 157(2-3), pp. 501-508 (2010).
Galli, et al., "Polypropylene: 44 Years Young! The Challenge for the 21st Century," Metalorganic Catalysts for Synthesis and Polymerization, pp. 14-29 (1999).
Ghiotto, et al., "Rapid evaluation of catalysts and MAO activators by kinetics: what controls polymer molecular weight and activity in metallocene/MAO catalysts?," Dalton Transactions 42(25), pp. 9040-9048 (2013).
Giro, et al., "Using artificial intelligence methods to design new conducting polymers," Materials Research 6(4), pp. 523-528 (2003).
Goncalves, et al., "Applications of Artificial Neural Networks in Chemical Problems," Artificial Neural Networks—Architectures and Applications, pp. 203-223 (2013).
Gonzalez-Ruiz, et al., "Kinetic modeling of slurry propylene polymerization using rac—ET(Ind)2ZrCl2/MAO," AIChE Journal 52(5), pp. 1824-1835 (2006).
Guo, et al., "Kinetics and mechanism of metallocene-catalyzed olefin polymerization: Comparison of ethylene, propylene homopolymerizations, and their copolymerization," Journal of Polymer Science Part A: Polymer Chemistry 55(5), pp. 867-875 (2017).
Herrmann, et al., "The First Example of an Ethylene-Selective Soluble Ziegler Catalyst of the Zirconocene Class," Angewandte Chemie 28(11), pp. 1511-1512 (1989).
Hildenbrand, et al., "The Formation of Terminal Double Bonds in Vinyl Chloride Polymerization," Journal of Macromolecular Science: Part A—Chemistry 17(7), pp. 1093-1106 (1982).
Himmelblau, "Applications of artificial neural networks in chemical engineering," Korean Journal of Chemical Engineering 17(4), pp. 373-392 (2000).
Holscher, et al., "Explanation of the Different Reaction Behaviors of Bridged and Unbridged Cationic Single Component Zirconocene Catalysts in MMA Polymerizations:? a Density Functional Study," Macromolecules 35(21), pp. 8194-8202 (2002).
Hough, et al., "Application of machine learning to pyrolysis reaction networks: Reducing model solution time to enable process optimization," Computers & Chemical Engineering 104, pp. 56-63 (2017).
Hutley & Ouederni, "Polyolefins—The History and Economic Impact," Polyolefin Compounds and Materials, pp. 13-50 (2016).
Ibrehem, et al., "Mathematical Model and Advanced Control for Gas-phase Olefin Polymerization in Fluidized-bed Catalytic Reactors," Chinese Journal of Chemical Engineering 16(1), pp. 84-89 (2008).
Inkson, et al., "Monte Carlo Simulation for the Structure of Polyolefins Made with Two Metallocene Catalysts in a Batch Reactor," Macromolecules 39(14), pp. 4920-4931 (2006).
Irfan, et al., "Modeling of NH3—NO—SCR reaction over CuO/y-Al2O3 catalyst in a bubbling fluidized bed reactor using artificial intelligence techniques," Fuel 93, pp. 245-251 (2012).
Kaminsky & Spiehl, "Copolymerization of cycloalkenes with ethylene in presence of chiral zirconocene catalysts," Die Makromolekulare Chemie 190(3), pp. 515-526 (1989).
Kaminsky & Steiger, "Polymerization of olefins with homogeneous zirconocene/alumoxane catalysts," Polyhedron 7(22-23), pp. 2375-2381 (1988).
Kaminsky, "Zirconocene catalysts for olefin polymerization," Catalysis Today 20(2), pp. 257-271 (1994).
Kaminsky, et al., "Polymerization of Propene and Butene with a Chiral Zirconocene and Methylalumoxane as Cocatalyst," Angewandte Chemie 24(6), pp. 507-508 (1985).
Kawamura-Kuribayashi, et al., "An ab initio MO and MM study of homogeneous olefin polymerization with silylene-bridged zirconocene catalyst and its regio-and stereoselectivity," Journal of the American Chemical Society 114(22), pp. 8687-8694 (1992).
Kim & Hwang, "Isospecific Polymerization of Propylene By ansa-Zirconocene Diamide Compound Cocatalyzed by Mao," Kournal of Macromolecular Science Part A: Pure and Applied Chemistry 35(12), pp. 1987-2008 (1998).

(56) References Cited

OTHER PUBLICATIONS

Kito, et al., "Estimation of catalytic performance by neural network—product distribution in oxidative dehydrogenation of ethylbenzene," Applied Catalysis A: General 114(2), pp. L173-L178 (1994).

Kolthammer, et al., "Polymerization kinetics of octene-1 catalyzed by metallocene methylaluminoxane investigated with attenuated total reflectance fourier transform infrared (ATR-FT-IR) spectroscopy," Journal of Polymer Science Part A: Polymer Chemistry 30(6), pp. 1017-1026 (1992).

Krauledat & Brintzinger, "Isotope Effects Associated with a-Olefin Insertion in Zirconocene-Based Polymerisation Catalysts: Evidence for an a-Agostic Transition State," Angewandte Chemie 29(12), pp. 1412-1413 (1990).

Leite, et al., "Application of Artificial Intelligence Techniques for Temperature Prediction in a Polymerization Process," Chemical Engineering Transactions 24, pp. 385-390 (2011).

Lenton, et al., "Formation of Trivalent Zirconocene Complexes from ansa-Zirconocene-Based Olefin-Polymerization Precatalysts: An EPR- and NMR-Spectroscopic Study," Journal of the American Chemical Society 135(29), pp. 10710-10719 (2013).

Li, et al., "Application of Artificial Neural Networks for Catalysis: A Review," Catalysts 7(10), 306, 19 pages (2017).

Lin, et al., "Kinetics of Propylene Polymerization Using Bis(2-phenylindenyl)zirconium Dichloride/Methylaluminoxane," Journal of the American Chemical Society 122(46), pp. 11275-11285 (2000).

Liu, et al., "Kinetics of Initiation, Propagation, and Termination for the [rac-(C2H4(1-indenyl)2)ZrMe][MeB(C6F5)3]-Catalyzed Polymerization of 1-Hexene," Journal of the American Chemical Society 123(45), pp. 11193-11207 (2001).

Manic & Sabharwall, "Computational Intelligence as a Tool for Small Modular Reactors," ASME 2011 Small Modular Reactors Symposium, SMR2011-6544, pp. 299-310 (2011).

Martinez, et al., "Polymerization Activity Prediction of Zirconocene Single-Site Catalysts Using 3D Quantitative Structure—Activity Relationship Modeling," Organometallics 31(5), pp. 1673-1679 (2012).

Mohd Ali, et al., "Artificial Intelligence techniques applied as estimator in chemical process systems—A literature survey," Expert Systems with Applications 42(14), pp. 5915-5931 (2015).

Mohring & Coville, "Group 4 metallocene polymerisation catalysts: quantification of ring substituent steric effects," Coordination Chemistry Reviews 250(1-2), pp. 18-35 (2006).

Molga, et al., "Neural networks for modelling of chemical reaction systems with complex kinetics: oxidation of 2-octanol with nitric acid," Chemical Engineering and Processing: Process Intensification 39(4), pp. 323-334 (2000).

Moscato, et al., "GPC and ESI-MS Analysis of Labeled Poly(1-Hexene): Rapid Determination of Initiated Site Counts during Catalytic Alkene Polymerization Reactions," Journal of the American Chemical Society 132(41), pp. 14352-14354 (2010).

Moscato, et al., "Mechanistic Investigations into the Behavior of a Labeled Zirconocene Polymerization Catalyst," Organometallics 31(5), pp. 2097-2107 (2012).

Nakazaki & Inui, "Highly selective decomposition of methanol to syngas on nickel-based composite catalysts using an artificial intelligence control reactor system," Industrial & Engineering Chemistry Research 28(9), pp. 1285-1289 (1989).

Nandi, et al., "Reaction Modeling and Optimization Using Neural Networks and Genetic Algorithms: Case Study Involving TS-1-Catalyzed Hydroxylation of Benzene," Industrial & Engineering Chemistry Research 41(9), pp. 2159-2169 (2002).

Nayak & Gupta, "Multi-Objective Optimization of Semi-Batch Copolymerization Reactors Using Adaptations of Genetic Algorithm," Macromolecular Theory Simulations 13(1), pp. 73-85 (2003).

Paass, "Assessing and Improving Neural Network Predictions by the Bootstrap Algorithm," Advances in Neural Information Processing Systems 5, pp. 196-203 (1993).

Parkale, "Comparison of ANN Controller and PID Controller for Industrial Water Bath Temperature Control System using MATLAB Environment," International Journal of Computer Applications 53(2), pp. 1-6 (2012).

Pletcher, "Quantitative Comparative Kinetics of 1-Hexene Polymerization across Group IV Bis-Phenolate Catalysts," ACS Catalysis 6(8), pp. 5138-5145 (2016).

Polikar, et al., "Artificial intelligence methods for selection of an optimized sensor array for identification of volatile organic compounds," Sensors and Actuators B: Chemical 80(3), pp. 243-254 (2001).

Prakash, "Kinetic Modeling and Simulation of Metallocene Catalyzed Olefin Polymerization," Birla Institute of Technology and Science, 309 pages (2013).

Psaltis, et al., "A multilayered neural network controller," IEEE Control Systems Magazine 8(2), pp. 17-21 (1988).

Resconi, et al., "Chain transfer reactions in propylene polymerization with zirconocene catalysts," Topics in Catalysis 7(1-4), pp. 145-163 (1999).

Rieger & Janiak, "Concentration effects of methylalumoxane, zirconocene dichloride and trimethylaluminum in ethylene polymerization," Macromolecular Materials and Engineering 215(1), pp. 35-46 (1994).

Rizkin, et al., "Artificial Neural Network control of thermoelectrically-cooled microfluidics using computer vision based on IR thermography," Computers & Chemical Engineering 121, pp. 584-593 (2019).

Ruiz, et al., "Neural network based framework for fault diagnosis in batch chemical plants," Computers & Chemical Engineering 24(2-7), pp. 777-784 (2000).

Sadiku, et al., "Machine Learning in Chemical Industry," International Journal of Advances in Scientific Research and Engineering 3(10), pp. 12-15 (2017).

Santos, et al., "Application of Artificial Neural Networks in an Experimental Batch Reactor of Styrene Polimerization for Predictive Model Development," Chemical Engineering Transactions 32, pp. 1399-1404 (2013).

Sasaki, et al., "Application of a neural network to the analysis of catalytic reactions Analysis of NO decomposition over Cu/ZSM-5 zeolite," Applied Catalysis A: General 132(2), pp. 261-270 (1995).

Schwaller, et al., "'Found in Translation': predicting outcomes of complex organic chemistry reactions using neural sequence-to-sequence models," Chemical Science 9(28), pp. 6091-6098 (2018).

Soga & Kaminaka, "Polymerization of propene with zirconocene-containing supported catalysts activated by common trialkylaluminiums," Macromolecular Chemistry and Physics 194(6), pp. 1745-1755 (1993).

Song, et al., "The kinetics of propene and hexene polymerisation with [(SBI)ZrR] X-: evidence for monomer-dependent early or late transition states," Chemical Communications 5, pp. 542-543 (2004).

Song, et al., "Zirconocene-catalysed propene polymerisation: kinetics, mechanism, and the role of the anion," Macromolecular Symposia 213(1), pp. 173-186 (2004).

Song, et al., "Zirconocene-Catalyzed Propene Polymerization:? A Quenched-Flow Kinetic Study," Journal of the American Chemical Society 125(25), pp. 7641-7653 (2003).

Subramanyam & Sivaram, "Kinetics of hexene-1 polymerization using [(N,N'-diisopropylbenzene)-2,3-(1,8-napthyl)-1,4-diazabutadiene] dibromonickel/methylaluminoxane catalyst system," Journal of Polymer Science Part A: Polymer Chemistry 45(6), pp. 1093-1100 (2007).

Switzer, et al., "Kinetic Modeling of 1-Hexene Polymerization Catalyzed by Zr(tBu-ONNMe2O)Bn2/B(C6F5)3," Macromolecules 45(12), pp. 4978-4988 (2012).

Valeh-E-Sheyda, et al., "Application of Artificial Neural Networks for Estimation of the Reaction Rate in Methanol Dehydration," Industrial & Engineering Chemistry Research 49(10), pp. 4620-4626 (2010).

Wang, et al., "Synthesis and Structures of Cycloalkylidene-Bridged Cyclopentadienyl Metallocene Catalysts: Effects of the Bridges of Ansa-Metallocene Complexes on the Catalytic Activity for Ethylene Polymerization," Chemistry: A European Journal 11(2), pp. 669-679 (2005).

(56) References Cited

OTHER PUBLICATIONS

Woo & Tilley, "Dehydrogenative polymerization of silanes to polysilanes by zirconocene and hafnocene catalysts. A new polymerization mechanism," Journal of the American Chemical Society 111(20), pp. 8043-8044 (1989).

Xue & Ray, "Cell Detection in Microscopy Images with Deep Convolutional Neural Network and Compressed Sensing," Cornell University Computer Science, Computer Vision and Pattern Recognition, arXiv:1708.03307, 29 pages (2018).

Yasin, et al., "Effect of temperature on the isospecific propylene polymerization catalyzed by rac-dimethylsilylbis(2,4,6-trimethyl-1-indenyl)zirconium dichloride/methyl aluminoxane," Polyhedron 24(11), pp. 1262-1268 (2005).

Young & Ma, "Polymerization Kinetics and Modeling of Slurry Ethylene Polymerization Process With Metallocene/MAO Catalysts," Polymer-Plastics Technology and Engineering 41(4), pp. 601-618 (2007).

Yu, et al., "Alkynyl Ether Labeling: A Selective and Efficient Approach to Count Active Sites of Olefin Polymerization Catalysts," ACS Catalysis 9(4), pp. 3098-3103 (2019).

Zhang & Friedrich, "Artificial neural networks applied to polymer composites: a review," Composites Science and Technology 63(14), pp. 2029-2044 (2003).

Zhang, et al., "Artificial neural network-genetic algorithm based optimization for the immobilization of cellulase on the smart polymer Eudragit L-100," Bioresource Technology 101(9), pp. 3153-3158 (2010).

Zhao, et al., "Kinetics, polymer molecular weights, and microstructure in zirconocene-catalyzed 1-hexene polymerization," Journal of Polymer Science A: Polymer Chemistry 38(20), pp. 3802-3811 (2000).

* cited by examiner

METHOD AND APPARATUS FOR THE RAPID DISCOVERY AND DESIGN OF POLYMERIZATIONS

CROSS-REFERENCE TO RELATED APPLICATIONS

The present application claims the benefit of and priority to U.S. Provisional Patent Application 62/892,453 filed Aug. 27, 2019, which is incorporated by reference herein in its entirety.

BACKGROUND

Systems involving catalytic reactions can be highly complex and difficult to optimize. While for many situations it is possible to either derive first principles models or gain a robust understanding of a system through experimentation, it is not always practical to take this direct approach, especially for highly multidimensional systems like industrial reactors, predicting nanostructures in functional materials, or predicting outcomes of complex polymerization processes.

SUMMARY

Various aspects of the present solution can apply machine learning solutions to perform materials optimization and discovery, such as for more effectively characterizing polymers and catalysts used for polymer reactions. The present solution can be implemented to perform very fast thermal control of reactors of various scales, including but not limited to a microchemical reactor, enabling faster and more accurate time to setpoint than PID, with the ability to factor in multiple input parameters like heat capacity and flow rate of reactants and information about the ambient environment. The present solution can use neural networks for the prediction of catalytic models for various processes, such as a Ziegler-Natta alpha-olefin polymerization reaction, as well as reactions involving biodegradable or green polymers, polypeptides, cyclic peptides, or branched peptides, polyimides, fluorinated polymers, degradable aliphatic polyesters, and various other polymers. The use of these networks can enable the prediction of useful polymer characteristics and the reverse prediction of kinetic rate constants from observable data. The present solution can enable artificially intelligent micro-scale reactors with in situ characterization techniques to detect multiphase physical and chemical rate processes.

At least one aspect relates to a system including a reactor. The reactor at least one reactant provided to perform a reaction. The system includes one or more sensors configured to detect sensor data regarding the reaction. The system includes processing circuitry configured to receive the sensor data from the one or more sensors, apply one or more machine learning models to the sensor data to generate a measurement regarding at least one of the reaction or an activity of a catalyst used in the reaction, and control at least one of a temperature of the reactor, a flow rate of the at least one reactant, or a concentration of the at least one reactant responsive to the measurement.

At least one aspect relates to a method. The method can include receiving, by processing circuitry, sensor data regarding a reaction from one or more sensors that detect the sensor data by monitoring a reactor; applying, by the processing circuitry, one or more machine learning models to the sensor data to generate a measurement regarding at least one of the reaction or an activity of a catalyst provided in the reactor; and controlling, by the processing circuitry, at least one of a temperature of the reactor, a flow rate of at least one reactant of the reactor, or a concentration of the at least one reactant responsive to the measurement.

At least one aspect relates to a method. The method can include receiving, by processing circuitry, first sensor data regarding a first reaction from one or more sensors that detect the first sensor data by monitoring a reactor. The method can include applying, by the processing circuitry, one or more machine learning models to the first sensor data to generate a first measurement of activity of the first catalyst provided in the reactor. The method can include receiving, by the processing circuitry, second sensor data regarding a second reaction of a second catalyst and at least one reactant. The method can include generating, by the processing circuitry, a second measurement of activity of the second catalyst using the second sensor data. The method can include comparing, by the processing circuitry, the second measurement of activity to the first measurement of activity. The method can include selecting, by processing circuitry, one of the first catalyst or the second catalyst based on the comparison.

At least one aspect relates to a method. The method can include providing training data as input to a machine learning model, the training data comprising (1) a measure of catalytic activity of a reaction between at least one catalyst and at least one reactant and (2) at least one output parameter regarding at least one product generated by the reaction. The method can include causing the machine learning model to generate candidate output responsive to the training data, the candidate output comprising at least one candidate output parameter. The method can include evaluating the candidate output using an objective function. The method can include modifying the machine learning model responsive to the evaluation.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

Figure 1:
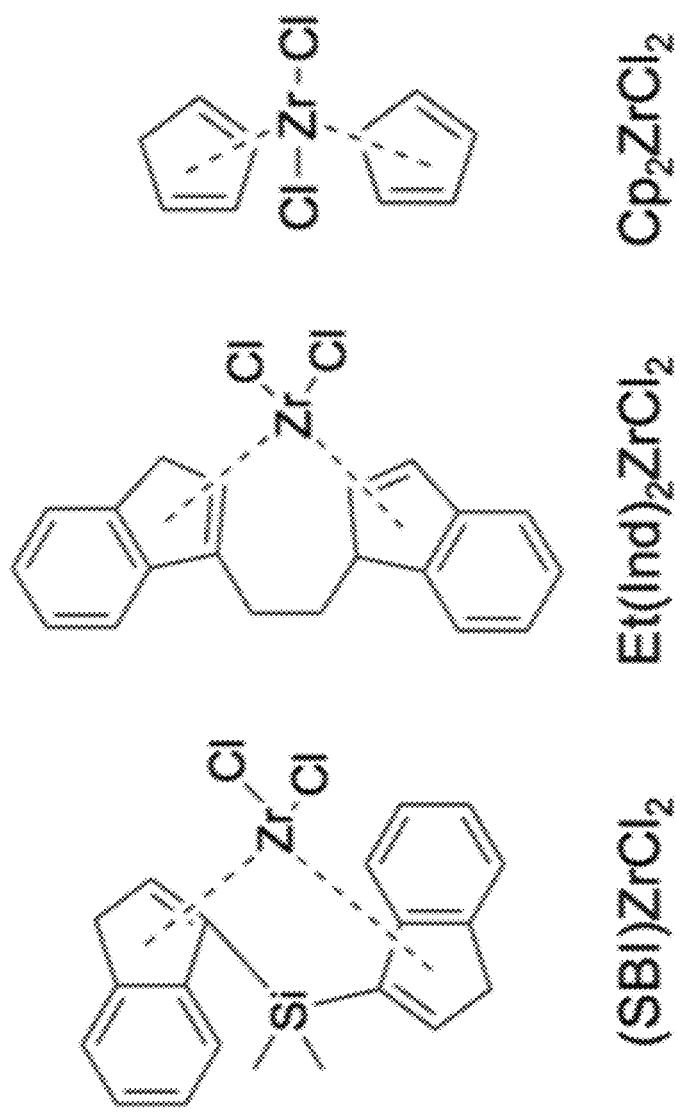
FIG. 1 illustrates three possible different types of zirconocene single-site polymerization catalysts.

Following below are more detailed descriptions of various concepts related to, and implementations of systems, methods, and apparatuses for rapid discovery and design of liquid-phase polymerization catalysts. The various concepts introduced above and discussed in greater detail below can be implemented in any of numerous ways, including in real-time monitoring and control of catalyst-driven reactions.

The present solution can implement machine learning to detect and analyze complex relationships between numerous variables computationally, including using artificial neural networks (ANNs), which can act as an analog to the human brain through a series of neurons bearing activation functions and threshold values, creating a feed-forward cascade of information. The present solution can apply machine learning to materials optimization and discovery, which can be useful since the formation and stability of these systems can be impacted by a large number of variables bearing complex relationships. The ANNs can be implemented to enable solutions involving fast computation, robust dynamics, a large amount of inputs, or any combination thereof. For example, ANNs can be used to perform fast thermal control of a microchemical reactor, enabling faster and more accurate time to setpoint than proportional-integral-derivative (PID) controllers, with the ability to factor in multiple input parameters like heat capacity and flow rate of reactants and information about the ambient environment. The present solution can use neural networks for the prediction of catalytic models, including for a Ziegler-Natta alpha-olefin polymerization reaction. The present solution can use neural networks for the prediction of non-catalytic models. The use of these networks can enable not only the prediction of useful polymer characteristics, but also allow for the reverse prediction of kinetic rate constants from observable data. The present solution can be used to discover and predict models for the generation of various polymers, including but not limited to biodegradable, or green, polymers, polypeptides, cyclic peptides, or branched peptides, polyimides, fluorinated polymers, degradable aliphatic polyesters, and polymers derived from natural sources (e.g., from biomass).

The present solution can be implemented with reactors of various scales, reaction types, and phases. For example, continuously stirred tank reactors, packed bed reactors (e.g., reactors having packed catalyst particles ranging from nanometers to millimeters in size), and plug flow reactors may be used. Microfluidic and millifluidic reactors may be used. Reactors may be used that range in scale based on reactor volume (e.g., from microliters to milliliters), volumetric flow rate (e.g., microliters per minute to milliliters per minute), or Reynolds number (e.g., laminar or turbulent flow). The reactors may be used to perform polymerization reactions in liquid phase, gas phase, or liquid-gas phase systems. The reactions may be performed at various temperatures from cryogenic to 1000 degrees Celsius, and various pressures ranging up to approximately 100 bar.

Accurately capturing non-steady-state behavior, very fast phenomena, and multiple data points from long runs can be difficult. For example, process controls can require highly specialized engineering and hardware with relatively high size, weight, power, and cost (SWAP-C) requirements. This may be the case for microreactor systems, which can allow for testing of different parameters much more quickly and efficiently than other reactors, while also offering benefits to mixing, heat transfer and the speed at which changes to the process can be made. The present solution can implement low-cost sensors SoC (System on a Chip) technologies (e.g., Arduino, Raspberry Pi), controller boards such as the Nvidia Jetson TK2, and big data and cloud computing to enabled more rapid and accurate detection and characterization of catalysts and catalysts parameters, such as reaction rate constants. The present solution can use convolutional neural networks to develop models to fit this data to enhance process control and optimization.

Chemistry for the Rapid Discovery and Design of Liquid-Phase Polymerizations

The present solution can be applied to various reaction processes, including catalytic and non-catalytic polymerization or depolymerization reactions. For example, the present solution can use metallocene alpha-olefin polymerization catalysts can exhibit characteristics that make them desirable for a range of applications. These catalysts can be active at ambient conditions. Poly(ethylene) and poly(propylene) processes may rely upon high temperature and pressure reactors, which not only use exponentially more energy, but also present safety concerns. These catalysts can allow for the tailoring of polymer properties, allowing for optimized materials. By tuning the properties of the catalyst molecule such as the stereochemistry, it becomes possible to make polymers with different tacticities and structure. Additionally, by modifying the activator composition, reaction concentrations and conditions, it becomes possible to tune the chain length, degree of branching and polydispersity of the resultant polymer. However, due to the complex synthesis pathways and fragile chemistry, these catalysts have only gained adoption in select parts of the olefin polymerization market. In general, metallocenes for polymerization of propylene, ethylene, 1-hexene and other alpha-olefins exhibit several stages in the catalytic cycle. The first step is initiation where a metal-alkyl bond is formed. Next is propagation where monomer units are inserted into the growing polymer chain, which could happen in a 1,2- or 2,1-direction. The final step is deactivation or termination. For kinetic determination and quantification of new catalysts three of these steps are largely important: initiation ($k_{init}$), propagation ($k_{prop}$) and spontaneous catalyst deactivation ($k_d$), which are for the most part universal between catalyst systems. The resultant polymer is either isotactic, atactic, or a mixture thereof depending on the chiral mixture of the catalyst. It can be difficult to detect relationships between reaction rate constants and polymer characteristics.

The present solution establishes a link between physically observable characteristics and reaction rate constants, allowing for ex situ analysis and interpretation of kinetic information. The ANN approach offers two benefits over first-principles calculations, the first being the ability to create solutions much quicker and with more limited computational power, and the second being the possibility of solving the system in reverse, which is not possible with the traditional differential mass balance approach. This has possible applications in industrial control and operation of catalytic polyolefin production processes in which marginal shifts in reaction characteristics can have a strong influence on commercially relevant properties. It also has potential application in research by removing the necessity to monitor labeled active sites or other markers in order to establish a link between the produced polymer and the catalytic cycle.

Reaction Mechanism

Figure 2:
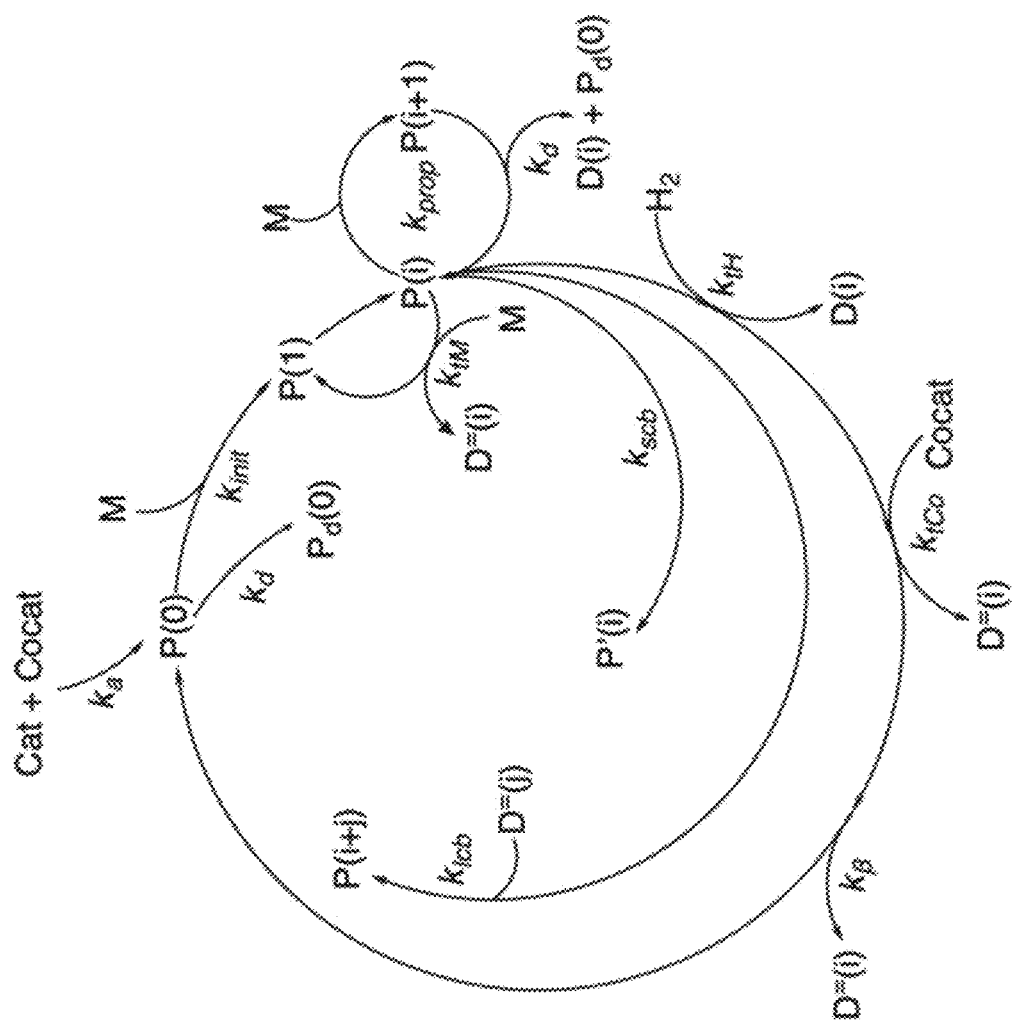
FIG. 2 illustrates a generalized catalytic cycle for polymerization of ethylene using a metallocene catalyst.

Various datasets for training machine learning models can be generated to relate the inputs and outputs of the models, such as for determining reaction rate constants from observable parameters. An example dataset is described below that can be based on a series of reaction steps and the resulting differential mass balances. The series of reaction steps can be seen below and in FIG. 2.

TABLE 1

Reaction steps

1. $Cat + Cocat \xrightarrow{k_a} P(0)$

2. $P(0) + M \xrightarrow{k_{init}} P(1)$

3. $P(i) + M \xrightarrow{k_p} P(i+1)$

4. $P(i) \xrightarrow{k_d} P_d(0) + D(i)$

5. $P(0) \xrightarrow{k_d} P_d(0)$

6. $P(i) + H_2 \xrightarrow{k_{tH}} D(i) + P(0)$

7. $P(i) + M \xrightarrow{k_{tM}} D^=(i) + P(1)$

8. $P(i) + Cocat \xrightarrow{k_{tCo}} D^=(i) + P(0)$

9. $P(i) \xrightarrow{k_\beta} D^=(i) + P(0)$

10. $P(i) + D^=(j) \xrightarrow{k_{tcb}} P(i+j)$

11. $P(i) \xrightarrow{k_{scb}} P'(i)$

Machine Learning Solutions for Rapid Discovery and Design of Polymerization Catalysts The present solution can implement machine learning solutions to improve catalyst discovery and design and reaction control. Machine Learning (ML) is a form of predictive analytics that can use a training dataset to develop a mathematical model for extrapolating conclusions from input data. Artificial Neural Networks (ANNs) are an example of ML that can be used to model complex systems and processes with multiple inputs and nonlinear behavior. The neural network can sum the values of inputs, normalize the inputs, and trigger a feedforward cascade to other neurons. For example, the ANN can be used to predict polymer characteristics from a multi-step metallocene alpha (olefin) polymerization reaction. As discussed above, the training set is derived from a series of first-principles differential species balances. The performance of the resulting ML solution can be compared with literary data to validate the ML solution (e.g., validate the model generated to relate polymer characteristics to observable parameters or rate constants).

Figure 3:
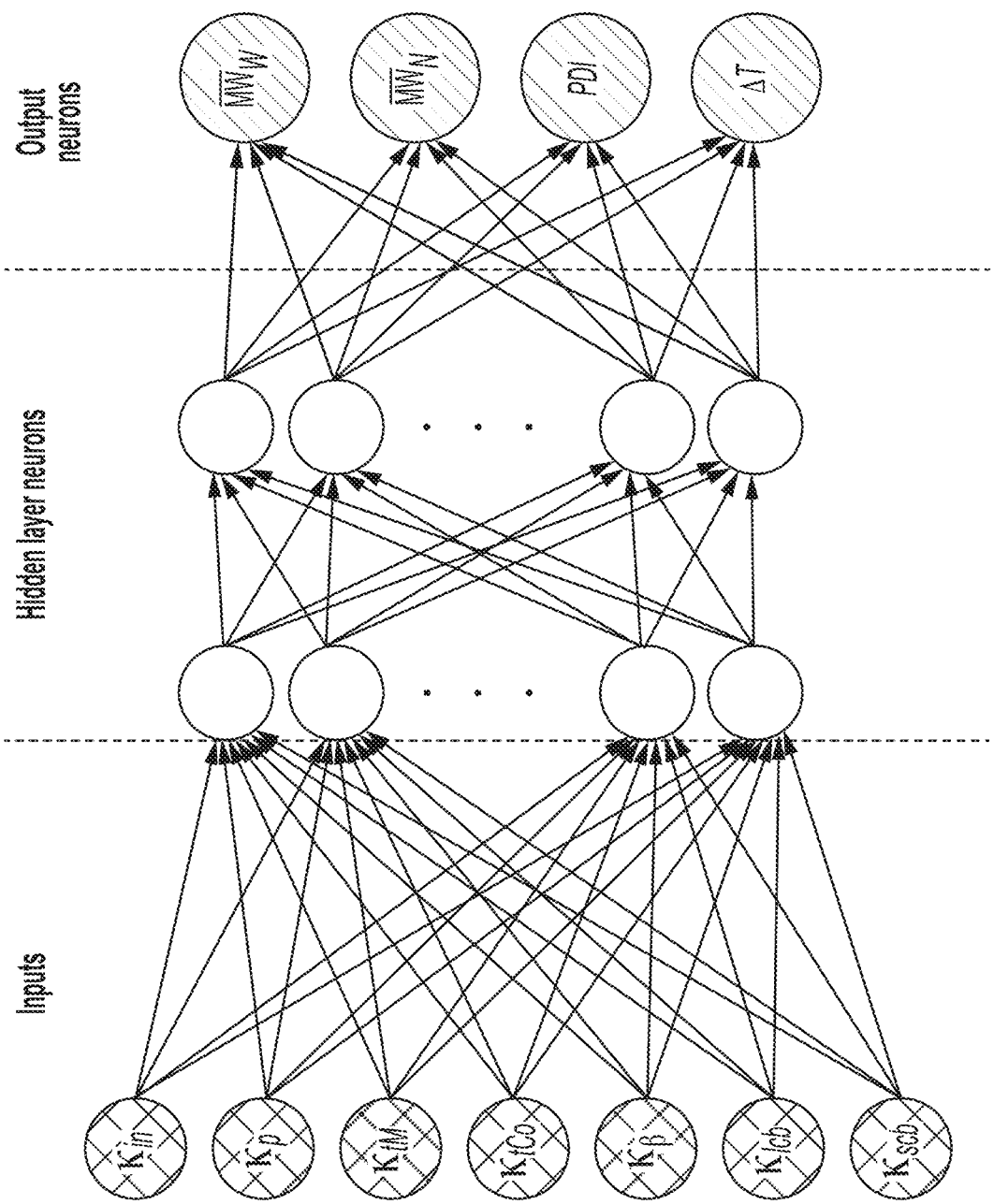
FIG. 3 illustrates a diagram of the network.
Figure 4:
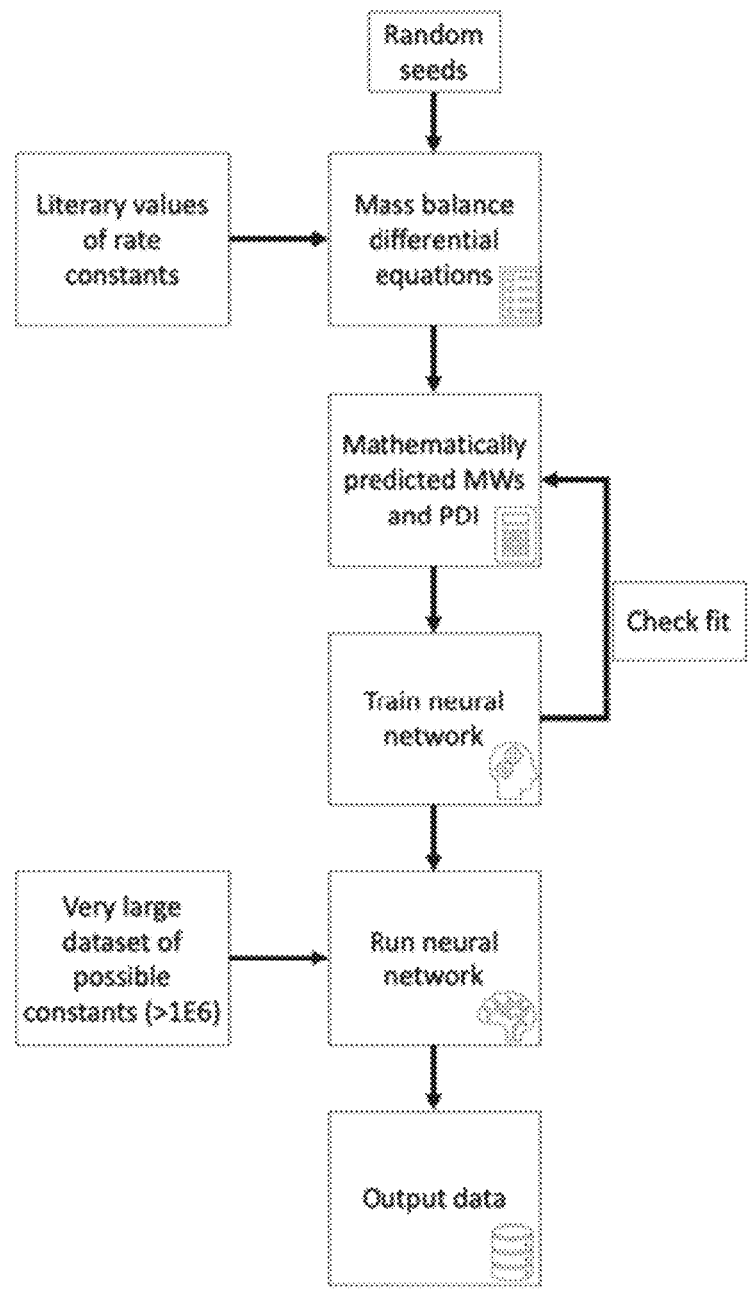
FIG. 4 illustrates dataflow for the experiment.

The present solution can train ANNs in various manners to enable the trained ANN to generate desired parameters, such as reaction rate constants, from observable parameters. An example of a process for training an ANN is described herein. To perform the ANN training, a dataset of 2000 possible combinations of reaction rate constants was formulated by combining constants from literature with random small up and down changes as an input to the differential species balances. The small changes were made as perturbations to the average literary values in order to adequately sample the entire space of possible reaction rate constants. The combination of rate constants was used in order to fully encompass the range of possible values. This moderately sized dataset was then used to train a neural network with 70% of the data being used for training, 15% for validation and 15% for testing. Since the initial conditions for the generation of the training set were already randomized, and the form of the distribution was known, retaining a 70/15/15 split was sufficient and it was not necessary to further randomize the samples or perform bootstrapping (Paass, 1993). The full dataset was used in the generation of all figures that follow. Based on a comparison of different training methods and numbers of hidden layer neurons a Levenberg-Marquardt training algorithm was used with 15 hidden neurons per layer and two layers. A full breakdown of the training results can be seen in FIG. 5. A diagram of the network can be seen in FIG. 3 and the dataflow for the experiment can be seen in FIG. 4. FIG. 3 shows a model of the neural network used for the prediction of polymer characteristics based on kinetic information about the catalyst. The network used two hidden layers each with 15 neurons and a Levenberg-Marquardt training algorithm, as this combination gave the highest fit fidelity. The network was used to predict the number and weight average molecular weights ($\overline{MW}_n$, $\overline{MW}_w$), polydispersity index (PDI) and adiabatic temperature change ($\Delta T$). FIG. 4 shows data flow for the computational experiment. A training dataset is first generated using a literary model with an augmented input matrix consisting of validated rate constants with randomly fluctuating seeds to augment the range of values. This dataset is used to train the neural network which is then in turn used to make predictions. All hidden layer weights and biases were computed automatically using the neural network training function in MATLAB. Overall, the training dataset was formulated using the 11-step reaction mechanism and then used to train the ANN, which in turn was checked using additional calculations and used to make predictions.

TABLE 2

Comparison of kinetic and polymer characteristic information for the polymerization of 1-hexene provided from the literature.

| Publication | Catalyst | Activator | Monomer | Kinetic information reported | $MW_w$ | $MW_n$ | Đ |
|---|---|---|---|---|---|---|---|
| Ghiotto, et al., 2013 | rac-Me$_2$Si(2-Me-Benze[e]Ind)$_2$ZrCl$_2$ | MAO | 1-hexane | $k_{init}$~3.8<br>$k_{prop}$~1.0<br>$k_d$~2-7 | ✓ | ✓ | ✓ |
| Moscato, et al., 2012 | (SBI)ZrCH$_2$SiMe$_2$(C$_6$H$_4$)NMe$_2$ | MeB(C$_6$F$_5$)$_3$ | 1-hexane | $k_{init}$~0.004<br>$k_{prop}$~1.0<br>$k_d$× | × | × | × |
| Moscato, et al., 2010 | rac-(SBI)Zr(Chrom)Me | MeB(C$_6$F$_5$)$_3$ | 1-hexane | $k_{init}$~0.0001<br>$k_{prop}$~0.4<br>$k_d$× | ✓ | — | ✓ |
| Song, et al., 2004a | (SBI)ZrCH$_2$SiMe)$_3$ | B(C$_6$F$_5$)$_4$ | 1-hexane | $k_{init}$×<br>$k_{prop}$ highly varied $k_d$× | × | × | × |
| Zhao, et al., 2000 | rac-(dimethylsilyl)bis(4,5,6,7-tetrahydro-1-indenyl)ZrCl$_4$ | MAO | 1-hexane | $k_{init}$×<br>$k_{prop}$×<br>$k_d$× | — | ✓ | ✓ |
| Liu, et al., 2001 | rac-(C$_2$H$_4$(1-indenyl)$_2$)ZrMe | MeB(C$_6$F$_5$)$_3$ | 1-hexane | $k_{init}$×<br>$k_{prop}$×<br>$k_d$× | × | × | × |
| Switzer, et al., 2012 | Zr(tBu-ONNMe$_2$O) | B(C$_6$F$_5$)$_3$ | 1-hexane | $k_{init}$~0.1<br>$k_{prop}$~11<br>$k_d$× | × | × | × |

Check marks (✓) represent data which is available in the publication, crosses (×) represent data which is not reported and "—" represents data interpolated using the correlation Đ = $MW_w/MW_n$.

The reaction steps enumerated above were used to construct a series of differential mass balances as can be seen below in Table 3.

TABLE 3

Differential Mass Balances

1. $r_{cat} = -k_a[\text{Cat}][\text{Cocat}]$
2. $r_{P(0)} = k_a[\text{Cat}][\text{Cocat}] - k_{in}[M][P(0)] - k_d[P(0)] + k_{tH}[H_2]\lambda_0^l + k_{tCo}[\text{Cocat}]\lambda_0^l + k_\beta\lambda_0^l$
3. $r_{P_d(0)} = k_d([P(0)] + \lambda_0^l)$
4. $r_{Cocat} = -k_a[\text{Cat}][\text{Cocat}] - k_{tCo}[\text{Cocat}]\lambda_0^l$
5. $r_M = -k_{in}[M][P(0)] - k_p[M]\lambda_0^l - k_{tM}[M]\lambda_0^l$
6. $r_{H_2} = -k_{tH}[H_2]\lambda_0^l$
7. $r_{P(i)} = -k_p[M][P(i)] + k_p[M][P(i-1)] - k_d[P(i)] + k_{tH}[H_2][P(i)] - -k_{tM}[M][P(i)] - k_{tCo}[\text{Cocat}][P(i)] - k_\beta[P(i)] - k_{lcb}[P(i)]\lambda_0^= - k_{scb}[P(i)]$
8. $r_{D(i)} = k_d[P(i)] + k_{tH}[H_2][P(i)]$
9. $r_{D^=(i)} = k_{tM}[M][P(i)] + k_\beta[P(i)] + k_{tCo}[\text{Cocat}][P(i)] - k_{lcb}[P(i)]\lambda_0^=$
10. $r_{P(i+j)} = k_{lcb}[P(i)]\lambda_0^=$
11. $r_{P'(i)} = k_{scb}[P(i)]$ These balance equations are then used to derive the moments of chain length distribution (CLD) for living ($\lambda_0^l, \lambda_1^l, \lambda_2^l$), dead ($\lambda_0, \lambda_1, \lambda_2$), and dead with terminal double bond ($\lambda_0^=, \lambda_1^=, \lambda_2^=$) polymer chains. Living polymer chains are ones which are still actively polymerizing, dead chains are no longer polymerizing and dead with terminal double bond chains have a double bond at or proximal to the end of the chain.

The number average and weight average molecular weights are computed from the moments of chain length distributions.

$$\overline{M_n} = 28.05 * (\lambda_1^l + \lambda_1 + \lambda_1^=)/(\lambda_0^l + \lambda_0 + \lambda_0^=) \qquad 1$$

$$\overline{M_W} = 28.05 * (\lambda_2^l + \lambda_2 + \lambda_2^=)/(\lambda_1^l + \lambda_1 + \lambda_1^=) \qquad 2$$

$$\overline{M_N} = \overline{M_W}/\overline{M_n} \qquad 3$$

This methodology can be used to determine other parameters of interest such as polymerization rate and the number of long and short chain branches in an average polymer chain. The adiabatic temperature change can be calculated as $T = ([-\Delta H_{Rx}(T_0)]X)/(\Sigma_{i=1}^n \Theta_i C_{P_i})$, where T is the temperature, $-\Delta H_{Rx}$ is the exotherm of reaction, $T_0$ is the initial temperature, X is the conversion, and $\Sigma_{i=1}^n \Theta_i C_{P_i}$ is the weighted average heat capacity of the solution.

This analysis can be applied to a homogeneous, well-mixed, adiabatic batch reactor, which allows for the separation of kinetic and transport phenomena in the analysis, which can remove dependence on a specific reactor system.

Upon generating the training dataset and a validation set, the network was trained and the quality of the fit was analyzed. Neural network predictions were made for the Weight Average Molecular Weight ($\overline{MW}_w$, $M_w$), Number Average Molecular Weight ($\overline{MW}_N$, $M_N$), Polydispersity Index (PDI, Đ) and the adiabatic temperature change. The rate of activation was assumed very fast and constant between all the trials, consistent with the work of Prakash et al. discussed above. Statistical analysis was performed on this data to verify the suitability of the ANN modeling approach to polymerization data. For the polymer characteristics prediction network, it was observed that the experimental (ANN-predicted) values closely matched the theoretically predicted (species balance-based) targets. A fit regression plot for the network can be seen in FIG. 5, along with a comparison of different network architectures.

Figure 5:
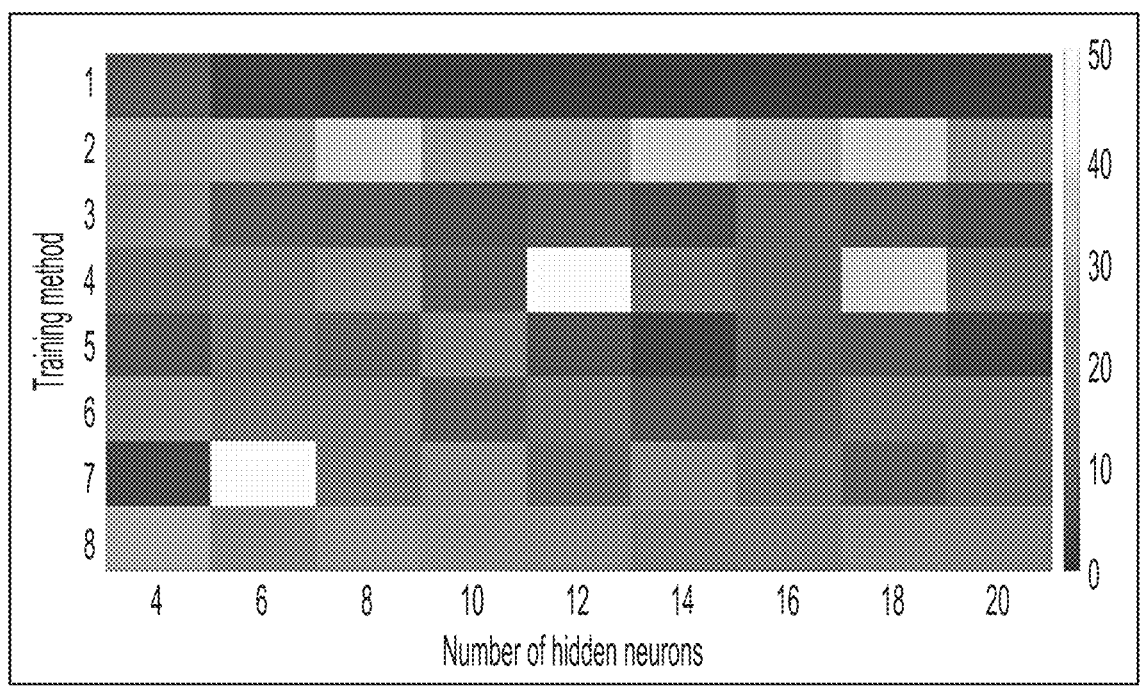
FIG. 5 illustrates a comparison of different training algorithms for the neural network with different numbers of hidden layer neurons, with the fit indicated as the Mean Square Error.
Figure 5:
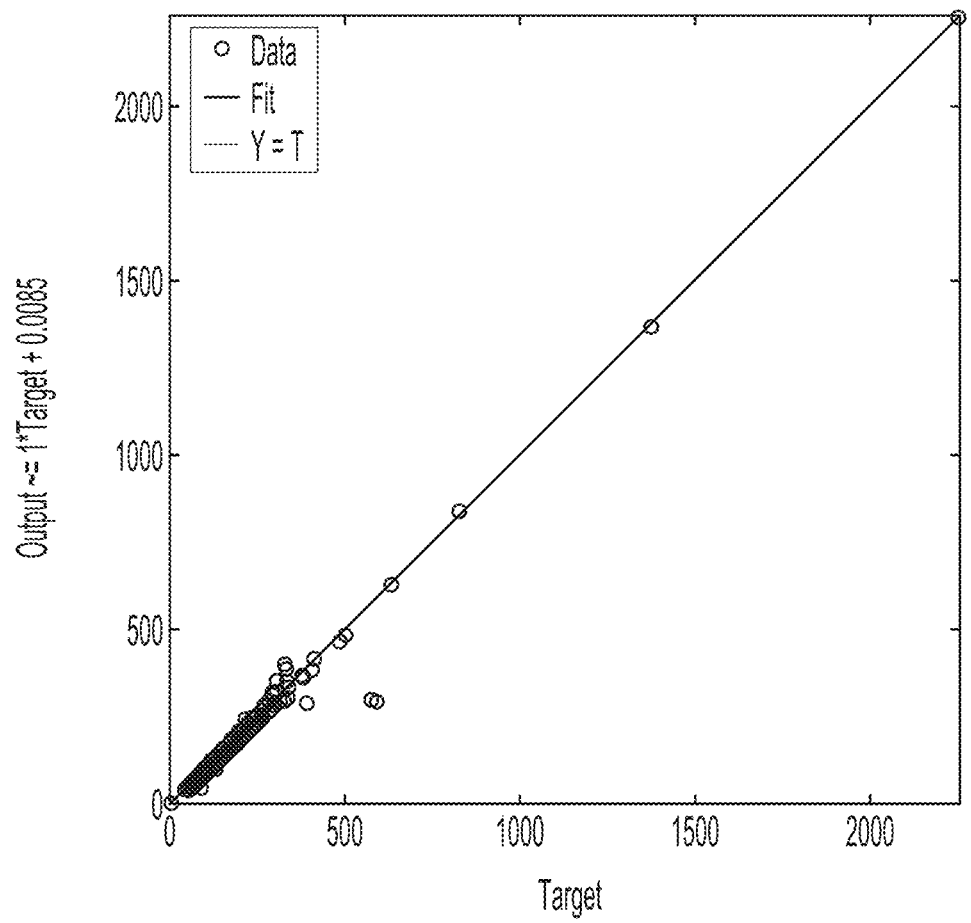

FIG. 5 shows a comparison of different training algorithms for the neural network with different numbers of hidden layer neurons, with the fit indicated as the Mean Square Error (lower is better). Algorithms: 1=Levenberg-Marquardt (Damped Least Squares), 2=quasi-Newton backpropagation, 3=Resilient backpropagation (RProp), 4=Scaled conjugate gradient backpropagation, 5=Conjugate gradient backpropagation with Fletcher-Reeves updates, 6=Conjugate gradient backpropagation with Powell-Beale restarts, 7=Conjugate gradient backpropagation with Polak Ribiére updates, 8=One-step secant backpropagation. (Bottom) Regression plot displaying the network inputs versus targets. This plot shows the predictive quality of the neural network as derived from the training function in MATLAB, using an equally-weighted combination of all the fitted factors, thus showing overall network fit quality. Fit quality (R-value) for validation and test datasets was 0.9987.

It is observed that for ΔT, Ð and MW the ANN predictions lies in overall good agreement with the first-principles differential special balance model. Next, basic statistical tests analysis was conducted on all the output parameters. In Table 4 it can be seen that overall the network represents the data with an $R^2$ value of 0.9987 between all the output data points. A P-test indicates a value of zero, meaning that the null hypothesis is statistically false. Finally, a Kolmogorov-Smirnov (KS) test is carried out on the data, returning a value of 1, indicating that the data does not in a whole represent a normal distribution. In Table 5 it is observed that the Root Mean Square Error (RMSE) between the predicted and target values lies within a relatively tight error band.

TABLE 4

Statistical test characteristics for overall ANN fit quality.

| Statistical test | value |
|---|---|
| $R^2$-value | 0.9987 |
| P-test | 0 |
| KS-test | 1 |

TABLE 5

RMSE fit characteristics for ANN output.

| Data point | RMSE | RMSE(percent) |
|---|---|---|
| $\overline{MW}_W$ | 0.8518 | 0.2599 |
| $\overline{MW}_n$ | 1.6977 | 0.2705 |
| Ð | 0.1118 | 5.8411 |
| Adiabatic ΔT | 7.9865 | 0.3535 |

The ANN was used to generate a very large sample range of possible kinetic parameters and to test the effects these would have on the measured parameters. A set of values was generated for $k_{init}$, $k_{prop}$, and $k_d$ and the neural network was run over this range, holding the other parameters constant. A study of the different permutations leads to the data in FIGS. 6-8. Analysis of these figures allows for interpretation of the experimental space and for a quick visual way to assess the impacts of different combinations of parameters.

Figure 6:
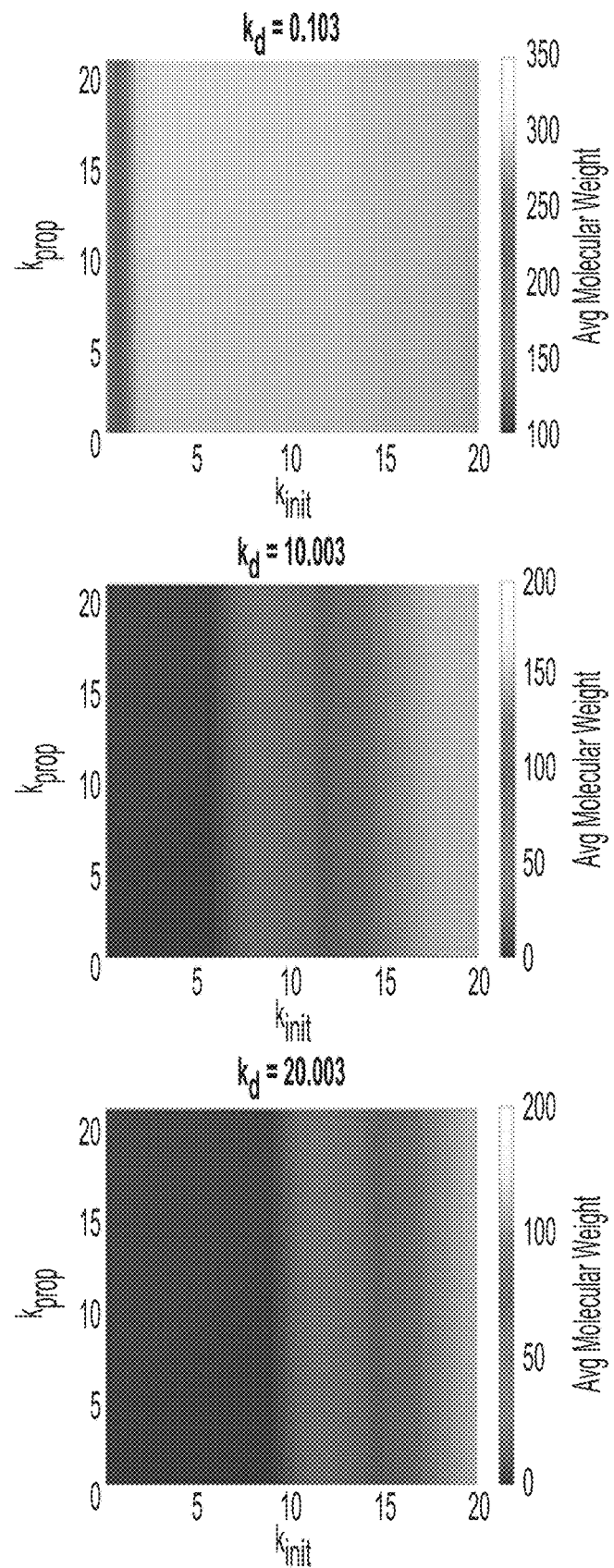
FIG. 6 shows heatmaps for $\overrightarrow{MW}_N$ ($\times 10^2$) over a range of $k_{init}$, $k_{prop}$, and $k_d$.
Figure 7:
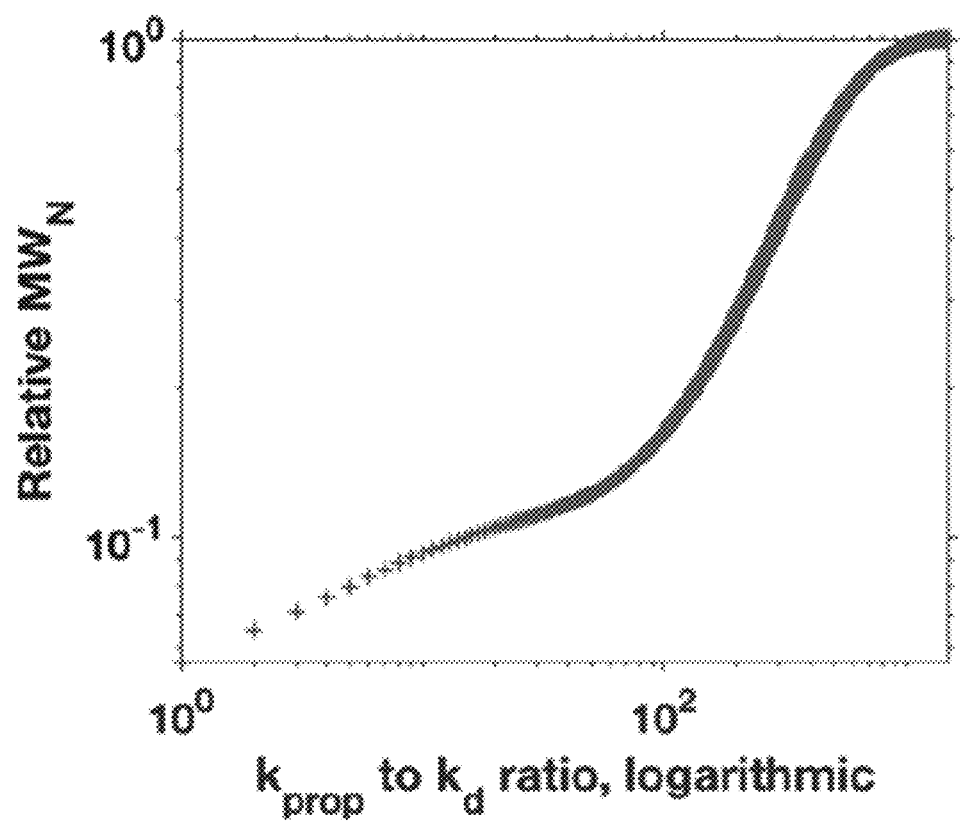
FIG. 7 shows a correlation between the relative number average molecular weight (MW divided by maximum MW) to the ratio of the rate constants of propagation and chain death.

FIG. 6 shows heatmaps for $\overline{MW}_N$ (×10²) over a range of $k_{init}$, $k_{prop}$, and $k_d$. In FIG. 6 the effect of the various kinetic constants on MW can be seen, with the top plot indicated a low $k_d$, then the middle a medium $k_d$ and the bottom a high $k_d$, all over the same range of $k_{init}$ and $k_{prop}$. These results suggest that lower values of $k_{init}$ result in a lower average molecular weight, with having a strong inverse correlation to molecular weight. FIG. 7 shows a correlation between the relative number average molecular weight (MW divided by maximum MW) to the ratio of the rate constants of propagation and chain death. A positive correlation is observed, indicating that relatively higher values of $k_{prop}$ result in larger chain lengths.

Figure 8:
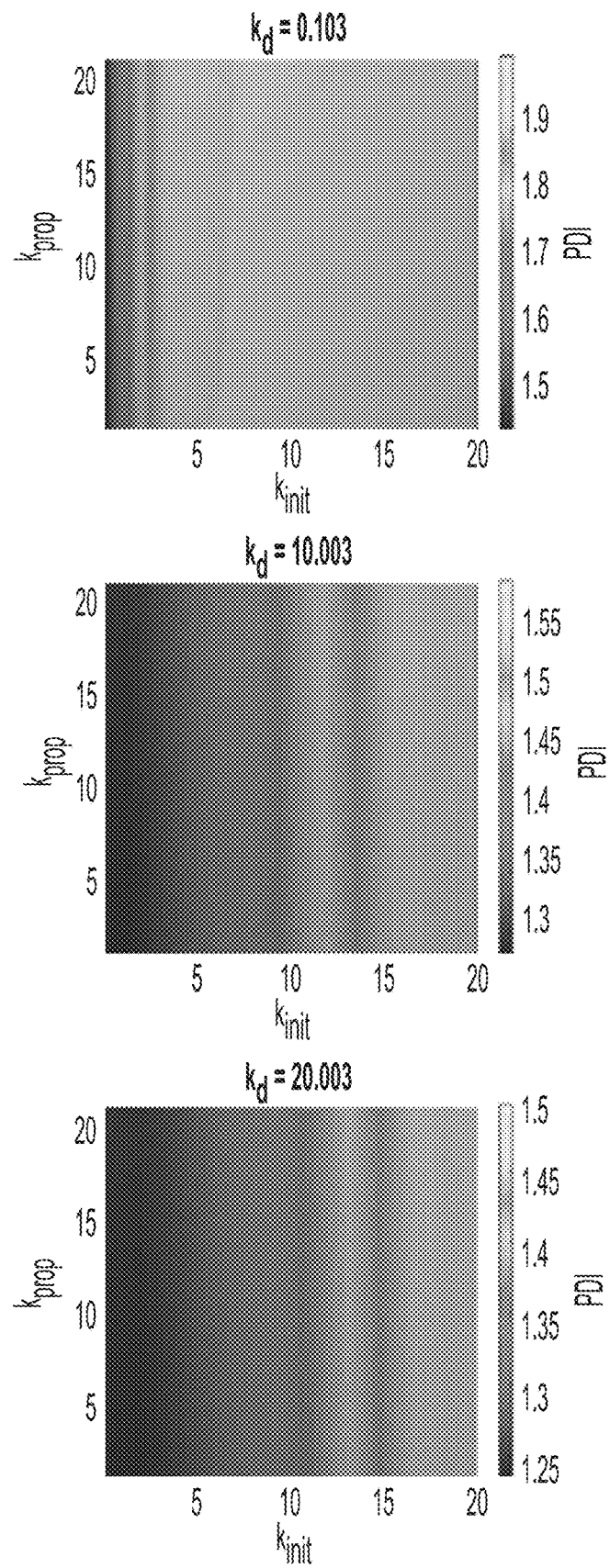
FIG. 8 shows heatmaps for D over a range of $k_{init}$, $k_{prop}$, and $k_d$.

FIG. 8 illustrates results of analysis of the Ð. For example, FIG. 8 shows heatmaps for Ð over a range of $k_{init}$, $k_{prop}$, and $k_d$. It is observed that as the rate of initiation increases the Ð also increases, with an inverse correlation being seen for the death rate of chains. It is also observed that the rate of propagation has little effect on the Ð, which is mainly a function of the initiation rate.

Figure 9:
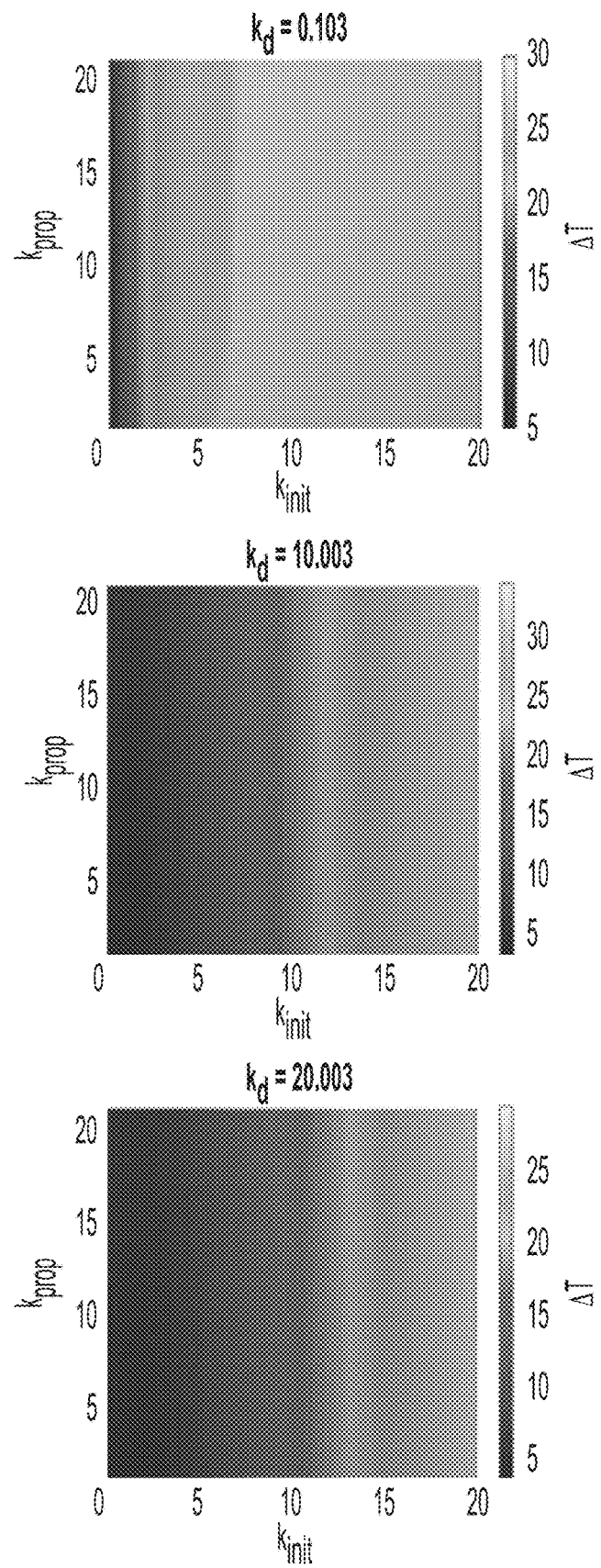
FIG. 9 shows heatmaps for adiabatic temperature change over a range of $k_{init}$, $k_{prop}$, and $k_d$.

FIG. 9 illustrates the effect of the different parameters on the final adiabatic temperature of the reactor. For example, FIG. 9 shows heatmaps for adiabatic temperature change over a range of $k_{init}$, $k_{prop}$, and $k_d$ The maximum temperature changes are seen at high rates of propagation, which can be explained because as the chain is growing more π bonds are being converted to σ bonds, releasing large amounts of energy. As the initiation rate increases, the final temperature also appears to increase, as more new chains are being nucleated. Finally, as the death rate increases the temperature drops off quickly, as relatively more active catalyst is being removed from the system and more of the monomer remains unreacted.

Reverse Prediction Training and Fit Characterization

Figure 10:
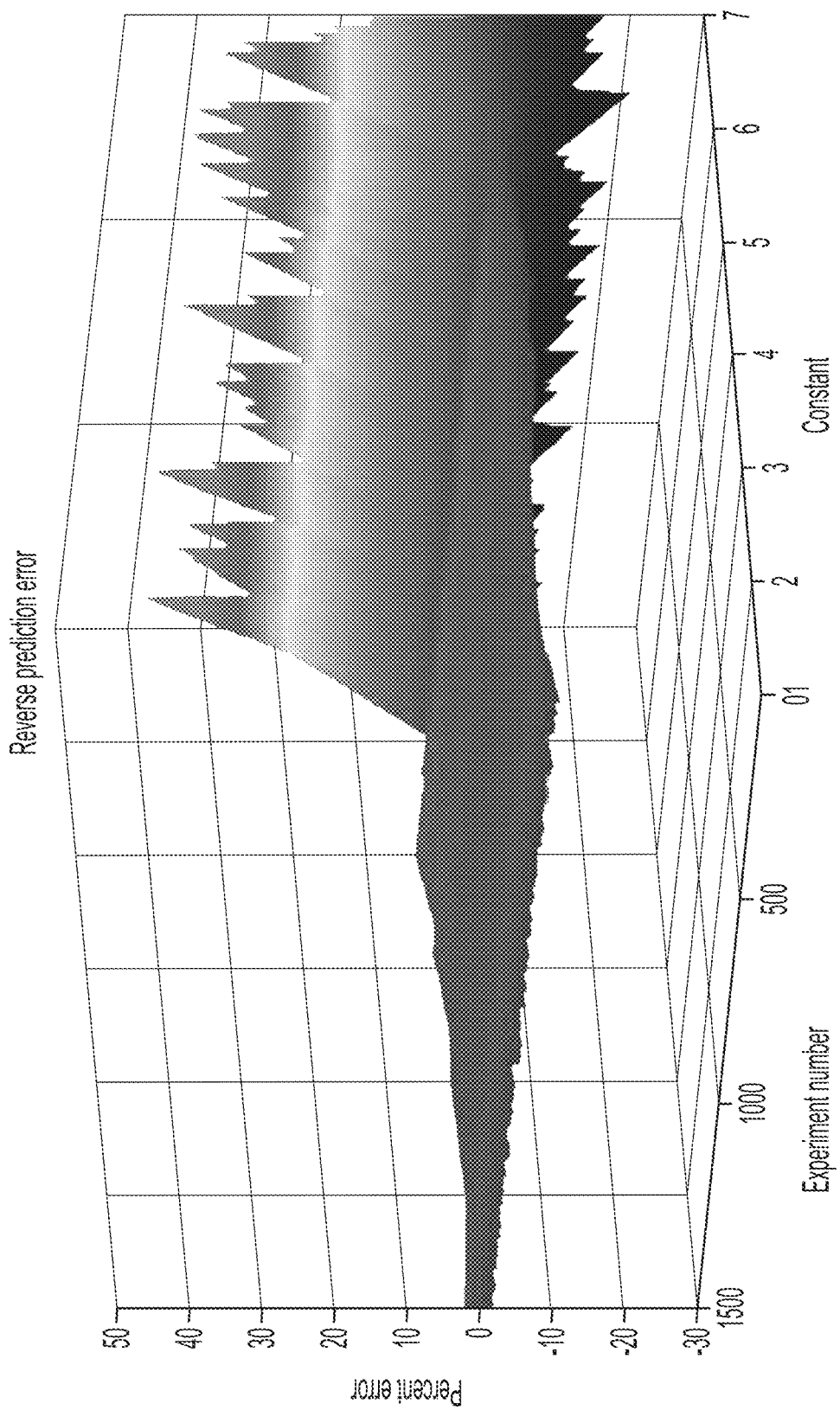
FIG. 10 shows reverse prediction percent error for an ANN versus the constants (in order $k_{init}$, $k_{prop}$, $k_d$, $k_{tM}$, $k_{tCo}$, $k_\beta$, and $k_{lcb}$ and the experiment number.

The present solution can train a machine learning model (e.g., neural network) to predict a possible combination of kinetic parameters given the molecular weight and Ð of a sample. The utility of this approach is that kinetic information can be deduced from parameters which can be measured ex situ. Accordingly, the present solution can enable detection of kinetic information from observable parameters in R&D and production environments where it may be impossible to monitor the concentrations of intermediates in the reaction cycle and derive kinetic rate constants. Due to the inherent multistep nature of the reaction mechanism (seen in FIG. 2), the ability to predict rate constants from observable parameters may be useful for optimizing catalyst turnover, or producing polymer with consistent characteristics. The overall network fit results for an example of this approach can be seen in Table 6, with the dataset passing the P and KS tests and having $R^2$-value of 0.9755. Furthermore, the RMSE for the various kinetic parameters, as seen in Table 7, indicates that in some examples, for all the parameters except the rate constant for Long Chain Branching ($k_{lcb}$), the errors are within a plausible margin. A surface plot of the prediction errors among different variables can be seen in FIG. 10. FIG. 10 shows reverse prediction percent error for an ANN versus the constants (in order $k_{init}$, $k_{prop}$, $k_d$, $k_{tM}$, $k_{tCo}$, $k_\beta$, and $k_{lcb}$ and the experiment number. It is observed that $k_{lcb}$ has the largest error. As with RMSE it is observed that for $k_{lcb}$ (long chain branching) the error is larger than for the other parameters, and the prediction has a stochastic nature to it. This constant may be harder to predict because of the implicit nature of how a long chain branching event can only occur when an activated polymer strand encounters a strand with a terminal double bond.

TABLE 6

Statistical tests for reverse-trained network.

| Statistical test | value |
|---|---|
| $R^2$ | 0.9755 |
| P-test | 0 |
| KS-test | 1 |

TABLE 7

First parameters for reverse-trained network.

| Data point | RMSE | RMSE(percent) |
|---|---|---|
| $k_{init}$ | 0.0627 | -1.1780 |
| $k_{prop}$ | 0.0004 | 0.3357 |
| $k_d$ | 0.0365 | -0.6604 |
| $k_{tM}$ | 0.0749 | -1.3561 |
| $k_{tCo}$ | 0.1155 | -1.9876 |

TABLE 7-continued

First parameters for reverse-trained network.

| Data point | RMSE | RMSE(percent) |
| --- | --- | --- |
| $k_\beta$ | 0.0120 | −0.4038 |
| $k_{lcb}$ | 0.9954 | −14.4118 |

The reverse training method may be improved in quality by introducing more variables into the prediction algorithm, including the number of branched polymers, rate of polymerization, etc.

Reaction Rate Constant Prediction from Incomplete Data

The present solution can use a trained ANN for the prediction of kinetic rate constants from observable parameters which can be measured ex situ. Data was analyzed for catalysts used in publications to derive kinetic rate constants from observable and recorded parameters and demonstrate the viability of the methodology. A neural network was trained that has weight average molecular weight, number average molecular weight and D as inputs and the kinetic rate constants for initiation and propagation as outputs, essentially the reverse of the network constructed above. Neural network training was updated using adaptive learning and data from entries one and three from Table 2, and data was simulated for values from one and five. This was performed because the previous analysis assumed poly(propylene) production and the entries in Table 2 are for poly(hexene), demonstrating the adaptability of this approach. The reverse trained network was then used to predict theoretical rate constants given experimental outcomes based on the training dataset.

Figure 11:
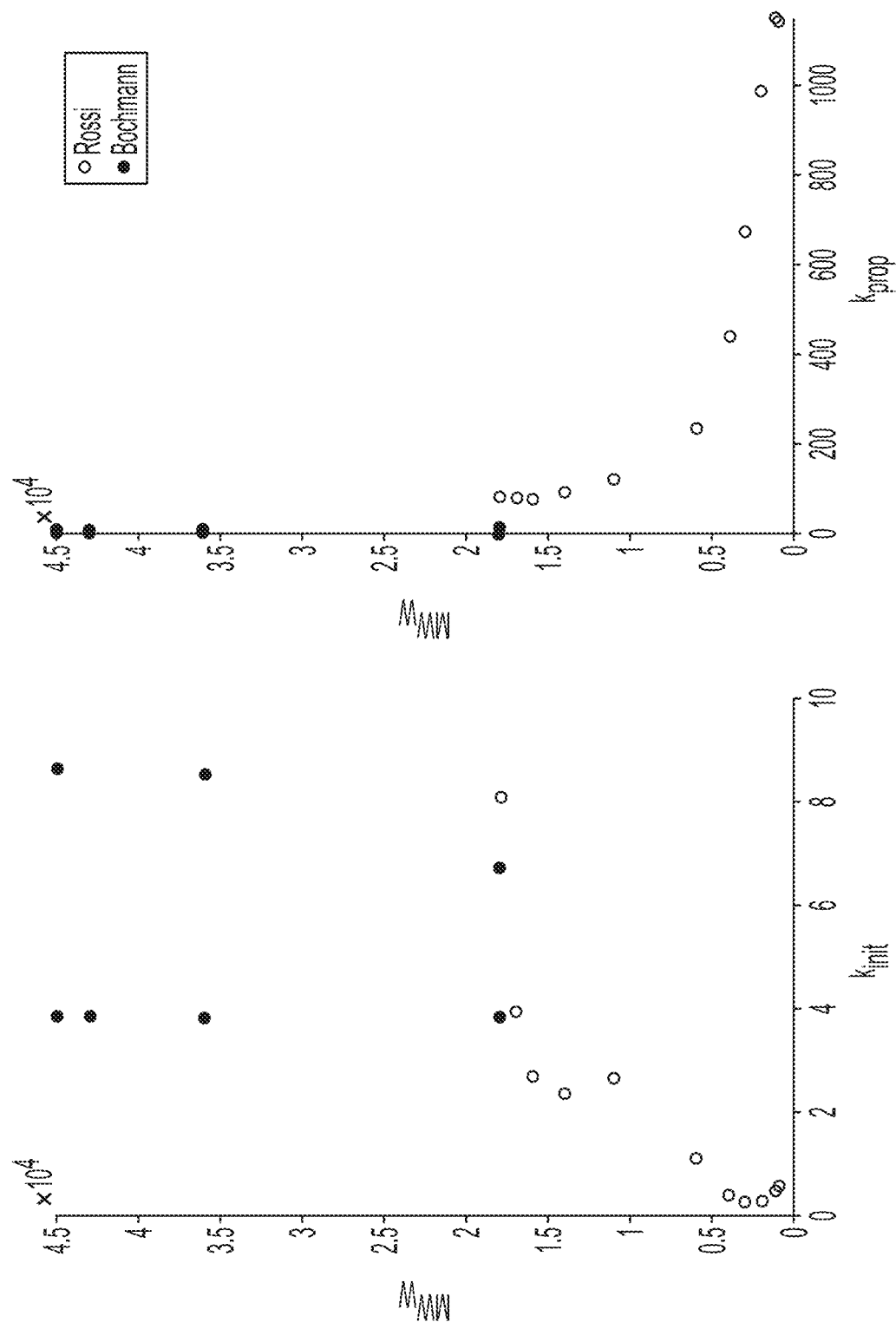
FIG. 11 shows reverse prediction for the kinetic rate constants for propagation and initiation.

Upon training the new network and adapting it using the two known values, the rest of the experimental values from the literature were run through the analysis and results for the kinetic rate constants of initiation, propagation and termination were computed. The results for the predictions of the kinetic rate constants based on the weight average molecular weight can be seen in FIG. 11. FIG. 11 shows reverse prediction for the kinetic rate constants for propagation and initiation. Green circles represent predicted data from (Zhao et al., 2000), blue circles represent predicted data from (Ghiotto et al., 2013), with the triangles representing confirmation data (each incorporated herein by reference).

Figure 12:
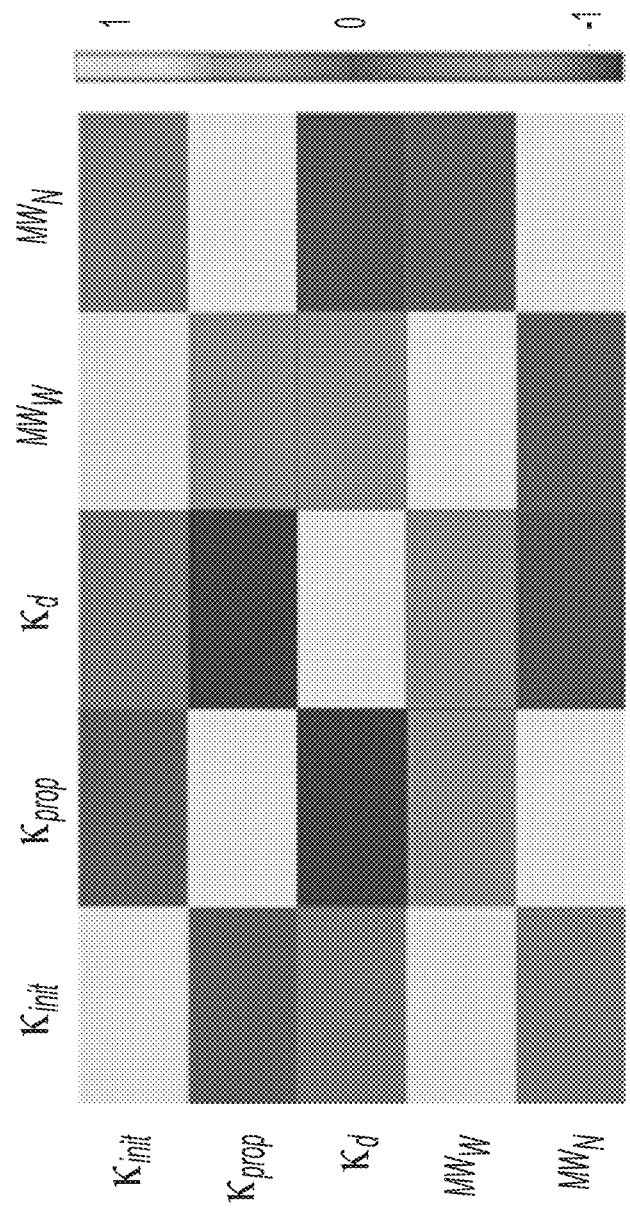
FIG. 12 shows the correlation coefficients between three key kinetic parameters and molecular weight information

A correlation matrix was computed between the three kinetic rate constants and the weight and number average molecular weights. The results from this calculation can be seen in FIG. 12 and show that there is a strong positive correlation between weight average molecular weight and the rate constant for initiation, and that the number average molecular weight is more impacted by the rate constant of propagation. FIG. 12 shows the correlation coefficients between three key kinetic parameters and molecular weight information, with yellow hues representing a strong positive correlation and blue hues a negative one. Finally the analysis indicates, as expected, that the rate constant of termination negatively impacts both of the molecular weights.

From analyzing the data produced by the forward training algorithm it is possible to make some conclusions about the catalyst. For example, it is possible to see that there is a region of suboptimal operation at low rates of $k_{init}$, $k_{prop}$, and $k_d$ where the D is higher than in neighboring regions. This has implications for industrial reactors and production systems where the D is desired to be low. It is also noted that at low $k_d$ the molecular weight increased. Additionally, it is observed that the number average molecular weight is related to the ratio between $k_{prop}$ and $k_d$. Overall this demonstrated that ANNs can be used as a tool to try to ascertain complex behavior from kinetic systems.

Upon analyzing the data from the reverse training methodology certain conclusions can also be drawn about this catalyst system, including the possible rate constants of initiation, propagation and termination given information of the weight average and number average molecular weights. Additionally, information was provided on the strength of relationships between these variables, which indicated that a high rate constant of initiation negatively impacts the number average molecular weight for polymer chains. It should be noted that due to the lack of consistent and complete data in the literature, combined with secrecy in industrial R&D, these conclusions are drawn only upon a few publications, and further studies are necessary to enhance understanding in this field.

By training a neural network to 'understand' an experimental space for a particular catalyst, it was demonstrated that various properties of the resultant polymer could be predicted. By using data from these predictions, scientists could more quickly narrow down desired experimental spaces, and engineers could better understand scaleup considerations, among other uses. The reverse training allows for the prediction of kinetic constants from observable data, which has implications for robust process control. By being able to monitor properties of a system in-line it becomes possible to have a robust link between the reaction mechanism and reactor performance. This could allow for safer reactor operation by bringing machine learning as a tool to prevent situations where reaction runaway could occur. An additional use could be for the fine-tuning of large industrial reactors as minor changes in the reaction regime can strongly influence the properties of the final polymer, which has implications for the marketability and industrial applicability. It is generally considered that polymers with longer chains and lower PDIs have better mechanical properties, and it is desirable to ensure production in the regime which optimizes these characteristics. It is also beneficial to understand the degree of branching, both long chain and short chain, as these characteristics also influence the final composition and properties of the polymer. This could also have applications in the development of new polymers and processing techniques for 3D printer filaments and other specialized applications. Overall the AI-based link between reaction rate constants and observable parameters has implications in different areas of polymer science and engineering.

Reactor Implementations

As described above, any of a variety of reactor systems operating in various phases and size scales may be used with and controlled by the machine learning models described herein. The reactor may be made from materials that are at least partially transparent to electromagnetic radiation in target wavelength bands (e.g., infrared radiation, visible light), such as glass, borosilicate, fused silica, or transparent ceramics, such as aluminum oxynitride (ALON), enabling the sensors (e.g., infrared sensors) to detect electromagnetic radiation resulting from the reactions being monitored. The reactor may include at least some materials that may not be necessarily required to be transparent to electromagnetic radiation, such as silicon, metal, silicon carbide, ceramics, or polymers (e.g., polydimethylsiloxane (PDMS), fluorinated polymers, polycarbonate, polyether ether ketone (PEEK), polytetrafluoroethylene (PTFE), perfluoroalkox alkane (PFA), fluorinated ethylene propylene (FEP), Teflon™, or Teflon™ AF, among others. The selection of materials may be based on parameters of the reactions to be performed, such as temperature or pressure.

Figure 13C:
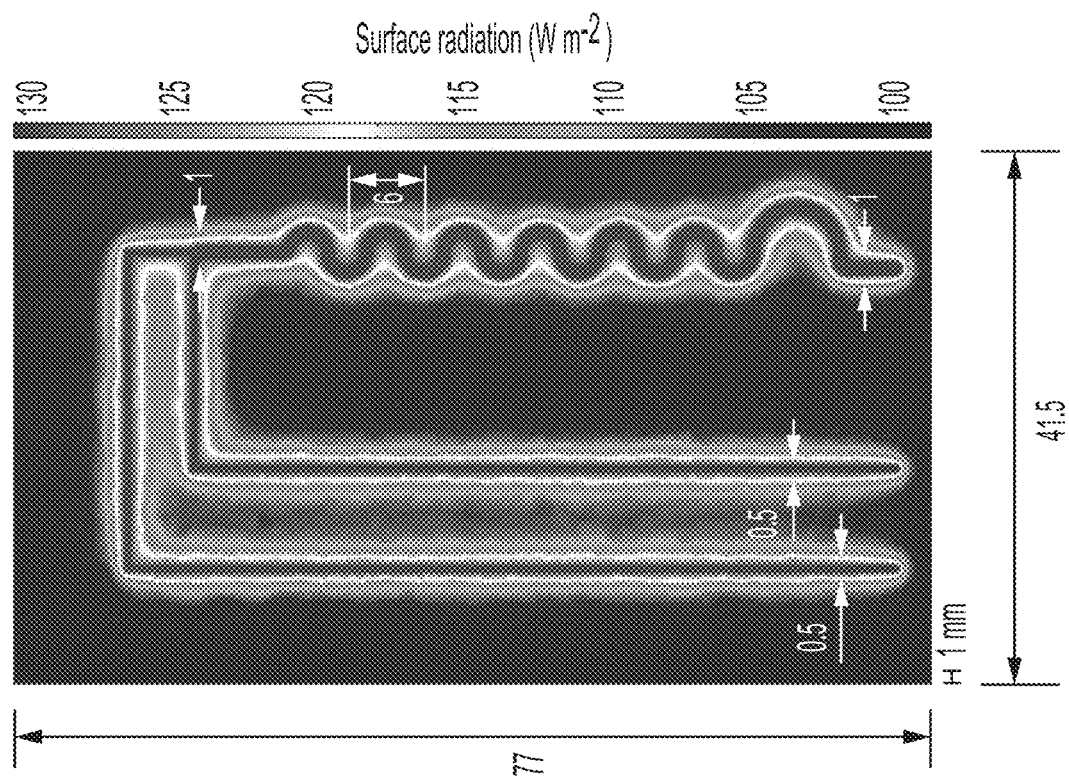
FIG. 13C illustrates a top view of microreactor showing channel and overall dimensions, R1 corresponds to a 1 mm hole used in conjunction with a viton o-ring.
Figure 13A:
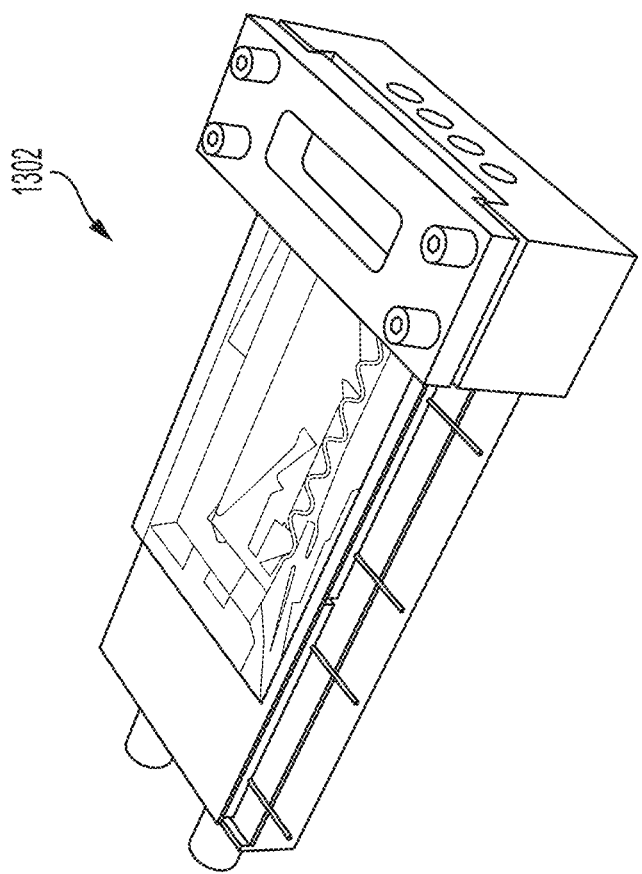
FIG. 13A illustrates a CAD rendering of the microreactor platform used showing the reactor, stainless steel compression chuck, Peltier modules and liquid cooling block, fluid connections for reagent feeds are on the right side of the reactor, and liquid cooling circulation connections are on the left.
Figure 13B:
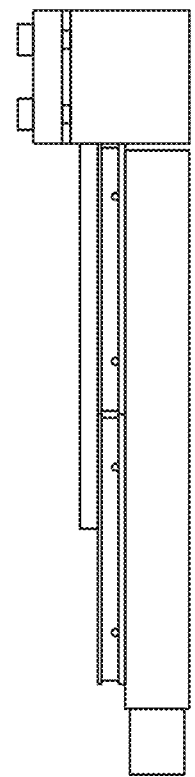
FIG. 13B illustrates a side view of microreactor and chuck.

FIG. 13A shows an example of a reactor platform 1302 (e.g. microreactor platform, millireactor platform, microfluidic device, millifluidic device etc.) used showing the reactor, stainless steel compression chuck, Peltier modules and liquid cooling block, fluid connections for reagent feeds are on the right side of the reactor, and liquid cooling circulation connections are on the left. The figure shows a water cooler block, electrical connections, bottom check, fluidic connections, top chuck, screws, o-rings, reactor chip, and Peltier cells. FIG. 13B shows a side view of microreactor and chucks. FIG. 13C shows a top view of microreactor showing channel and overall dimensions, R1 corresponds to a 1 mm hole used in conjunction with a viton o-ring. The reactor geometry is also shown with units in mm. Additionally, the results of a finite element simulation show an approximately 30 W/m$^2$ difference in flux with a 20 K temperature gradient.

The reaction platform integrates an upstream manifold and mixing section, displacement pump with reservoirs, an IR-transparent reactor, thermal control system and IR camera. The reaction platform can deliver a continuously variable experimental composition to the reactor, while also controlling mixing and dispersion through flowrate.

The reactor was fabricated by photopolymerization of VeroClear™ resin (Stratasys, Rehovot, Israel) on an Objet30 Pro™ printer with a dimensional accuracy of 16 μm an tensile strength of at least 50 MPa. The top surface of the reactor was composed of Poly IR® 1 (Fresnel Technologies, Fort Worth TX). After printing the reactor was cleaned first in a sodium hydroxide bath (2% solution, under sonication, 40° C., overnight), then repeatedly rinsed with toluene to remove any organic residues and deionized water before being dried under filtered nitrogen. The IR lens was cleaned with toluene and plasma etched for one hour. The reactor channels were masked off with hot wax and the top and bottom surfaces of the reactor were bonded using Loctite® 406™ ethyl cyanoacrylate adhesive. The assembly was then placed into a hydraulic press under 440 N of force for fifteen minutes. Finally the device was exposed to UV light overnight. The device was then heated to 50° C. to melt the wax, and rinsed repeatedly with toluene, acetone and DI water before being dried with nitrogen.

Reagents were prepared in a glovebox operating at <1 PPM $O_2$ and transferred in gastight syringes to the experiment. Syringes were then connected to a 6-inlet PFTE manifold (Cole-Parmer® EW-01356-17) which connected to a dosing pump (Cole-Parmer® EW-73120-38). The dosing pump fed into a 1.5 mL reservoir (Elveflow® Eppendorf® XS-2) which was also connected to an Elveflow® OB1 pump. The reagents would then flow through the reactor and to an output manifold which allows for sampling. All fluidic connections were made using 1/32 ID PTFE Teflon® tubing and the reactor was enclosed in a vacuum chamber to prevent IR interference and heat loss. During the beginning of a trial the respective manifold would be triggered, after which the dosing pump would transfer a preset volume of fluid to the reservoirs. The OB1 pump would then push this fluid through the reactor system using displacement via UHP $N_2$. This allowed for mixing different ratios of reagents in real time and for the application of automation.

Thermal control can be provided by two 61-watt Marlow® TR060-6.5-40 L thermoelectric modules connected to an Eaton D96115ACZ3 solid-state relay driven by an ATmega 2560 Arduino® at ~490 Hz and 8-bit resolution. Thermal contact with the reactor was provided by Protonix Series 7 thermal compound. Heat dissipation from the thermoelectric modules was through a liquid cooling block to a 360 mm radiator with three 120 mm fans operating at 1650 RPM, a small expansion tank and 12 volt circulating pump. The system is constructed in such a way as to enable either elevated temperature operation through switching the polarity of the thermoelectric modules, or cryogenic operation by replacing the radiator with a chiller.

The system can include a reactor. The reactor can include at least one reactant provided to perform a reaction. In some embodiments, the reactor includes at least one catalyst that can be used to perform the reaction with the at least one reactant. The at least one catalyst can include droplets of catalyst. The at least one reactant can include droplets of reactant. In some embodiments, the system can include a multiphase flow. The at least one reactant can include a first reactant of a first phase and a second reactant of a second phase, the second phase different from the first phase. For example, multiphase flow can include a gas-liquid flow, a gas-solid flow, a liquid-liquid flow, and a liquid-solid flow. The reactor can include one or more inlet manifolds to provide the at least one catalyst and the at least one reactant to the reaction. For example, the one or more inlet manifolds can supply the at least one catalyst and the at least one reactant to the reaction. The one or more inlet manifolds can supply multiple catalysts and multiple reactants to the reaction. In some embodiments, the at least one catalyst is a zirconocene. In some embodiments, the reaction produces an α-olefin. For example, the reaction can produce an α-olefin such as propene, 1-butene, 1-decene, or isobutylene.

The system can include one or more sensors configured to detect sensor data regarding the reaction. The sensor data can include molecular weight, polydispersity, or cross-linking. The sensor data can include a temperature of the reaction or a flow rate of the reaction. The sensor data can include dynamic light scattering data detected by a dynamic light scattering (DLS) sensor. The sensor can include nuclear magnetic resonance data detected by a nuclear magnetic resonance (NMR) sensor. The sensor can include high performance liquid chromatography data detected by a chromatography sensor. The one or more sensors can include an infrared sensor. The infrared sensor can detect thermal fluctuations of the reaction or the reactor. The reactor can include a microfluidic device. For example, the microfluidic device can include channels with a characteristic length scale on the order of tens or hundreds of microns. The reactor can include a millifluidic device. For example, the millifluidic device can include channels with a characteristic length scale on the order of tens or hundreds of millimeters.

The system can include processing circuitry configured to receive the sensor data from the one or more sensors, apply one or more machine learning models to the sensor data to generate a measurement of activity of the catalyst, and control at least one of a temperature of the reactor, a flow rate of the at least one reactant, or a concentration of the at least one reactant responsive to the measurement of activity of the catalyst. The processing circuitry can be configured to control the at least one of the temperature of the reactor, the flow rate of the at least one reactant, or the concentration of the at least one reactant to increase the measurement of activity to be greater than a threshold measurement of activity. The processing circuitry can be configured to use the machine learning model as a digital twin. A digital twin can include a process whereby a mathematic model (e.g., ANN) is used in lieu of a physical system to draw potentially relevant conclusions. The algorithm can run the machine learning model as a digital twin and use the results to find a probable maximum.

The system can be a portable system. For example, the reactor, the one or more sensors, and the processing circuitry can be portable, such as by being coupled with a local power supply. For example, the processing circuitry can include a miniaturized controller. The reactor, the one or more sensors, and the processing circuitry can be components of an autonomous system, such that power and materials for performing the reactions are included in the autonomous system (e.g., in a housing or other structure that supports the components of the system). For example, the system can be integrated into a device or system that includes self-propelled autonomous robotics. The system can be disposed in a transport case (e.g., Pelican® 1870) using an aluminum framing structure. The microreactor platform can be paired with infrared thermography for exotherm analysis, pumps, manifolds and associated process support and control infrastructure. The system can include a transport case with internal framework constructed using 1" T-slotted framing. Power supplies, pumps, manifolds, a reagent holder, robotic arm, and microreactor enclosure can be built into the framework. The system can be highly compact and portable while offering large flexibility for different types of chemical studies.

The case can include an integrated power and controls management strategy. The design criteria can include maximum portability and ease of adaptation. The box may only connected with a single power cable (110 V, 15 A), which supplies a protected power strip. The power strip can be connected to a series of transformers and DC rectifiers to the various low-voltage electronics in the box. The total power draw at standby can be ~20 watts and while operating can be ~75 watts, enabling power to easily be fed from a battery enabling off-grid operation. A single Li-ion 18650 can ensure safe and informed operation. The control panel can include a keyboard and mouse for interacting with the control software.

A premise of a high-throughput experimental station can be the ability to store and utilize numerous reagent combinations automatically and safely. A custom 3D printed reagent shelf can be fabricated with slots for standard vials. The slots can offer either the ability to hold the reagent with the septum facing up and the robotic arm piercing it with a needle, or the ability to insert needles form the bottom and have the robotic arm place the vials onto them. The first scenario can be used when a lower residence volume is desired, as there may not be need for an input manifold between the needle and reactor. The second case can be used when cross-contamination between the samples is a critical concern. Chemical waste can be collected in a 250 mL container equipped with a ¼-28 connection for chemically-resistant PTFE tubing. The container can be equipped with a carbon filter or exhaust tube to eliminate potential pressure buildup. Overall the reagent storage and management solution can be designed in such a way as to maximize the flexibility of the system for future studies.

The system can use a microreactor for fast and efficient experimentation with the chip lying at the center of the box and being interconnected with the various pumps and manifolds. The microreactor can have two parallel feed channels used to establish laminar flow and heat/cool the reagents as necessary. These channels can be followed by a micromixer section consisting of a series of radiused segments to encourage fluid mixing. The total volume of the micromixer section can be 60 μL, having a width of 1 mm and a depth of 2 mm.

The micromixer segment can encourage fast contact between the two phases, reducing the measured effects of mass transport and ensuring that the reaction runs in a reaction rate limited regime instead of a transport limited one. The chip can be fabricated on a photopolymerization 3D printer (Objet® 3D) and is bound to an IR transparent material (PolyIR® 1) for analysis by a thermal camera. The chip can then be connected to two Peltier thermoelectric modules (Marlow® TR060-6.5-40 L) and a liquid circulation water block. The entire assembly can be then bolted to miniature T-slotted framing which slots into the 3D-printed reactor enclosure. The reactor enclosure can provide a passthrough for the various fluidic tubes and wires while maintaining a vacuum to prevent IR interference and heat loss. Overall this reactor fabrication methodology can allow for maximal flexibility when redesigning reactors for different experiments and minimize the cost and labor that go into each chip.

A calibrated infrared camera (ICI® 9640P) can be contained within the reactor enclosure and can be used to analyze the heat produced in the reaction channel. Data from the camera can be fed over USB back to the control laptop.

Heat can be either removed or supplied to the Peltier thermoelectric modules by a standard liquid cooling system consisting of a pump, 360 mm radiator and fans. Liquid can be pumped from the pump reservoir to the liquid circulation block, through the radiator and back into the reservoir. The system can also be branched through a manifold to provide heat removal to future spectroscopic instruments or a high-power graphics card for tensor computing. Experiments performed in this study can be held at ambient temperature of 22.90° C.

A robotic arm (UARM Swift Pro) can be used to reconfigure the placement of the reagents on the shelf. The arm can be integrated with the LabVIEW® control software which can control its movements through a pre-configured matrix of reagent locations. The arm can include an open-source Arduino® microcontroller which can be expanded with computer vision capabilities. A suction cup or gripper can be used.

Chemical handling can be supplied by a set of manifolds (Cole-Parmer® EW-01356-17), dosing pumps (Cole-Parmer® EW-73120-38), a pressure driven pump (Elveflow® OB1) in a reconfigurable arrangement using standard ¼-28 fittings. This can enable maximum flexibility for performing different types of experiments and mixing various concentrations in real time. Using fluidic resistance the minimum achievable flowrate can be 10 μL/min and the maximum can be 2000 μL/min. This can correspond to a minimum residence time of 1.5 seconds and a maximum of ~5 minutes.

The entire setup can be built onto a modular 1" T-slotted framing chassis and can be placed into a Pelican® transport case. This can enable future expansion while also maintaining mobility and safety. All electrical and chemical components can be physically separated except for the Peltier modules and IR camera and the case is made of thick Polypropylene which can contain most leaks. The system can be operated in an open arrangement inside of a fume hood, or the top can be placed on the transport case and connected to local ventilation when a fume hood is not available. The case can be easily shipped or transported due to the small footprint and low weight, including by a UAV if necessary. Overall the system can be designed for maximum flexibility and applicability to both this and future studies.

Figure 14:
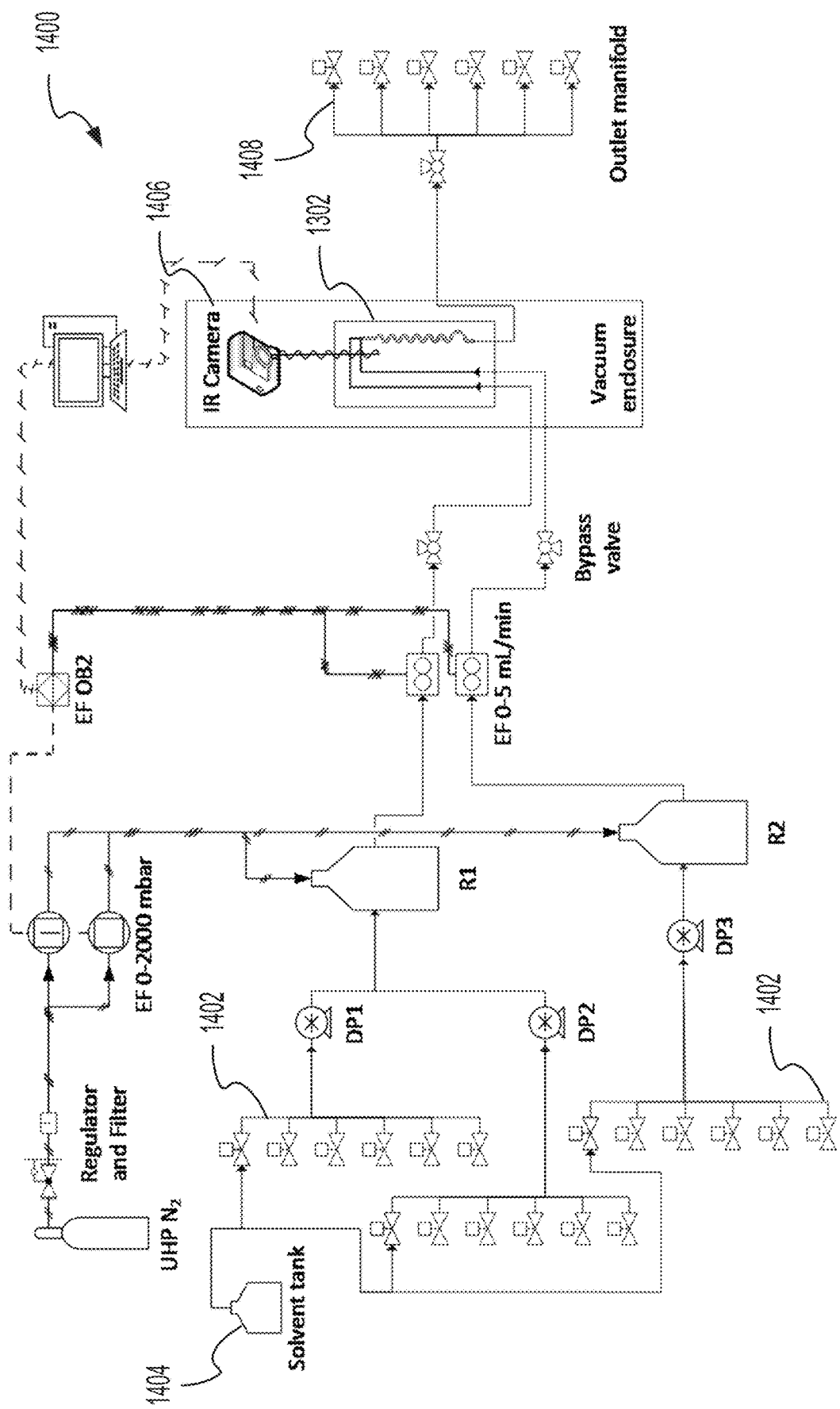
FIG. 14 illustrates a process flow diagram of the reactor system.

FIG. 14 shows a process flow diagram of the reactor system 1400. The reactor system 1400 includes the reactor platform 1302. An infrared (IR) camera 1406 can monitor a temperature of the reactor of reactor platform 1302. The reactor system 1400 can include one or more inlet manifolds 1402 upstream of the reactor platform 1302. A solvent tank 1404 can supply the inlet manifolds 1402 with solvent or reactants. Products of the reaction can be supplied to an outlet manifold 1408.

Monitoring and control of the experiment were accomplished using a calibrated infrared camera (ICI® 9640P) communicating via USB to MATLAB® R2019a. Each frame from the thermal camera was stored as a 640×480 matrix of double precision values which was easily amenable to numerical filtering and analysis. Fluidic control was accomplished through LabVIEW® 2018. Control of the feed solenoids was accomplished through an ATmega 2560 Arduino® microcontroller coupled with a bank of relays switching 12 volt DC from a generic 300 watt ATX-style power supply. The power to the system is interlocked through a 120-volt 30 amp electromechanical relay with an emergency disconnect button with all chemical-handing components being inside of a fume cabinet. Electrical interconnections are made through a Redco Audio® (Stratford, CT) snake box and shielded Cat5e cable.

Residence time distribution studies were carried out using a constant flow of water with acetone as the tracer. Fluid flow was provided by a Harvard Apparatus® PhD Ultra 2000 syringe pump and injection was performed using an Idex® 8125 Manual Injection Valve with a 50 µL injection volume. Detection of acetone in the reactor outlet was accomplished using an Ocean Optics® DH-2000-BAL UV-VIS-NIR light source coupled with an Ocean Optics® FLAME-S-UV-VIS-ES spectrometer measuring between 200-850 nm with a 600/300 grating.

IR thermography can be used to measure fluid temperature and two-phase flow patterns was developed. IR thermography can be been coupled with temperature frame processing methods to estimate heat distribution of chemical reactions along a channel in a microreactor.

Figure 15:
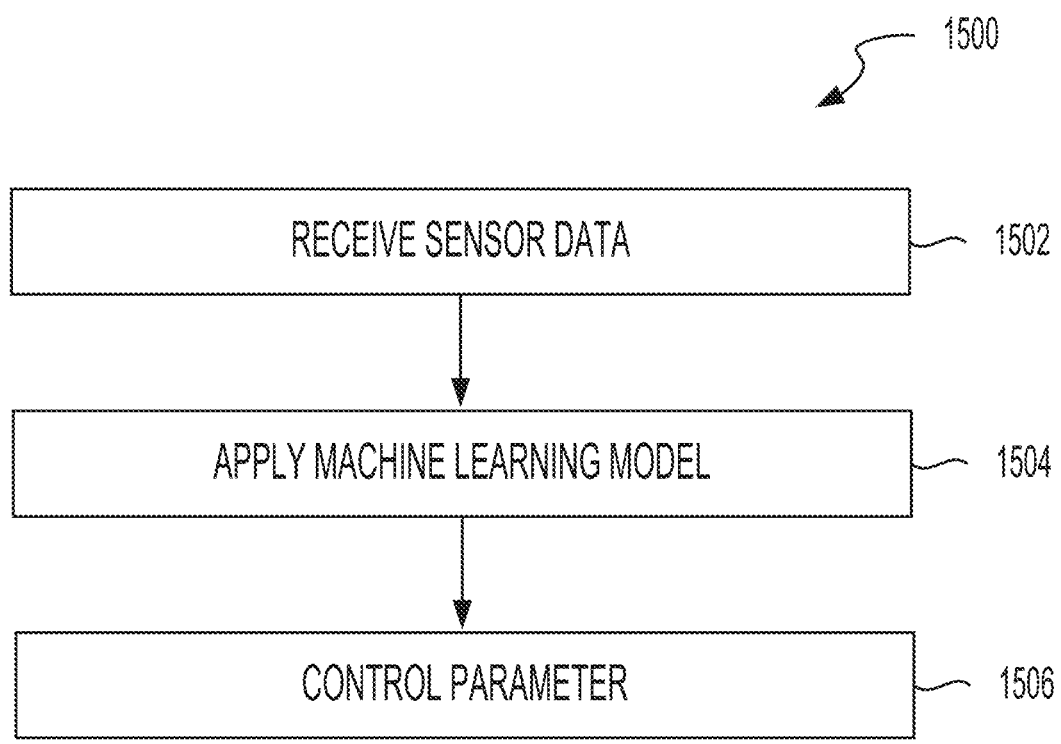
FIG. 15 illustrates a method of controlling parameters of a reactor, according to an example implementation.

FIG. 15 illustrates a method 1500 of controlling parameters of a reactor, according to an example implementation. The method 1500 can be implemented using various systems and devices described herein, such as the reactor platform 1302 and reactor system 1400. In brief summary, the method 1500 can include receiving sensor data (BLOCK 1502). The method 1500 can include applying one or more machine learning models (BLOCK 1504). The method 1500 can include controlling a parameter (BLOCK 1506).

The method 1500 can include receiving first sensor data (BLOCK 1502). The method can include receiving, by processing circuitry, first sensor data. The sensor data can include data regarding a first reaction from one or more sensors that detect the first sensor data by monitoring a reactor. For example, the one or more sensors can include an infrared camera to capture thermal information of a reaction. The infrared camera can monitor thermal fluctuations of the reaction. Data from the infrared camera can include reaction exotherm data, which can be used to interpret catalytic productivity. Catalytic productivity can be a metric for polymerization catalyst design. The sensor data can include molecular weight, polydispersity, or cross-linking. The sensor data can include a temperature of the reaction or a flow rate of the reaction. The sensor data can include dynamic light scattering data, nuclear magnetic resonance data or high performance liquid chromatography data. The dynamic light scattering data can be detected by a dynamic light scattering (DLS) sensor. The nuclear magnetic resonance data can be detected by a nuclear magnetic resonance (NMR) sensor. The high performance liquid chromatography data can be detected by various spectrometric devices.

The method 1500 can include applying one or more machine learning models (BLOCK 1504). The method can include applying one or more machine learning models to the sensor data to generate a measurement of activity of a catalyst provided in the reactor. For example, the one or more machine learning models can include various models described herein, such as one or more ANNs trained to generate the measurement of activity of the catalysts based on sensor data such as temperature, flow rate, and concentration.

The method 1500 can include controlling a parameter (BLOCK 1506). The parameter can include at least one of a temperature of the reactor, a flow rate of at least one reactant of the reactor, or a concentration of the at least one reactant responsive to the measurement of activity of the catalyst. The method can include controlling the parameter by the processing circuitry. The processing circuitry can be configured to control the at least one of the temperature of the reactor, the flow rate of the at least one reactant, or the concentration of the at least one reactant to increase the measurement of activity to be greater than a threshold measurement of activity. For example, the processing circuitry can be configured to increase, decrease, or maintain the temperature of the reactor to increase the measurement of activity to be greater than a threshold measurement of activity. The processing circuitry can be configured to increase, decrease, or maintain the flow rate of the at least one reactant to increase the measurement of activity to be greater than a threshold measurement of activity. The processing circuitry can be configured to increase, decrease, or maintain the concentration of the at least one reactant to increase the measurement of activity to be greater than a threshold measurement of activity.

Figure 16:
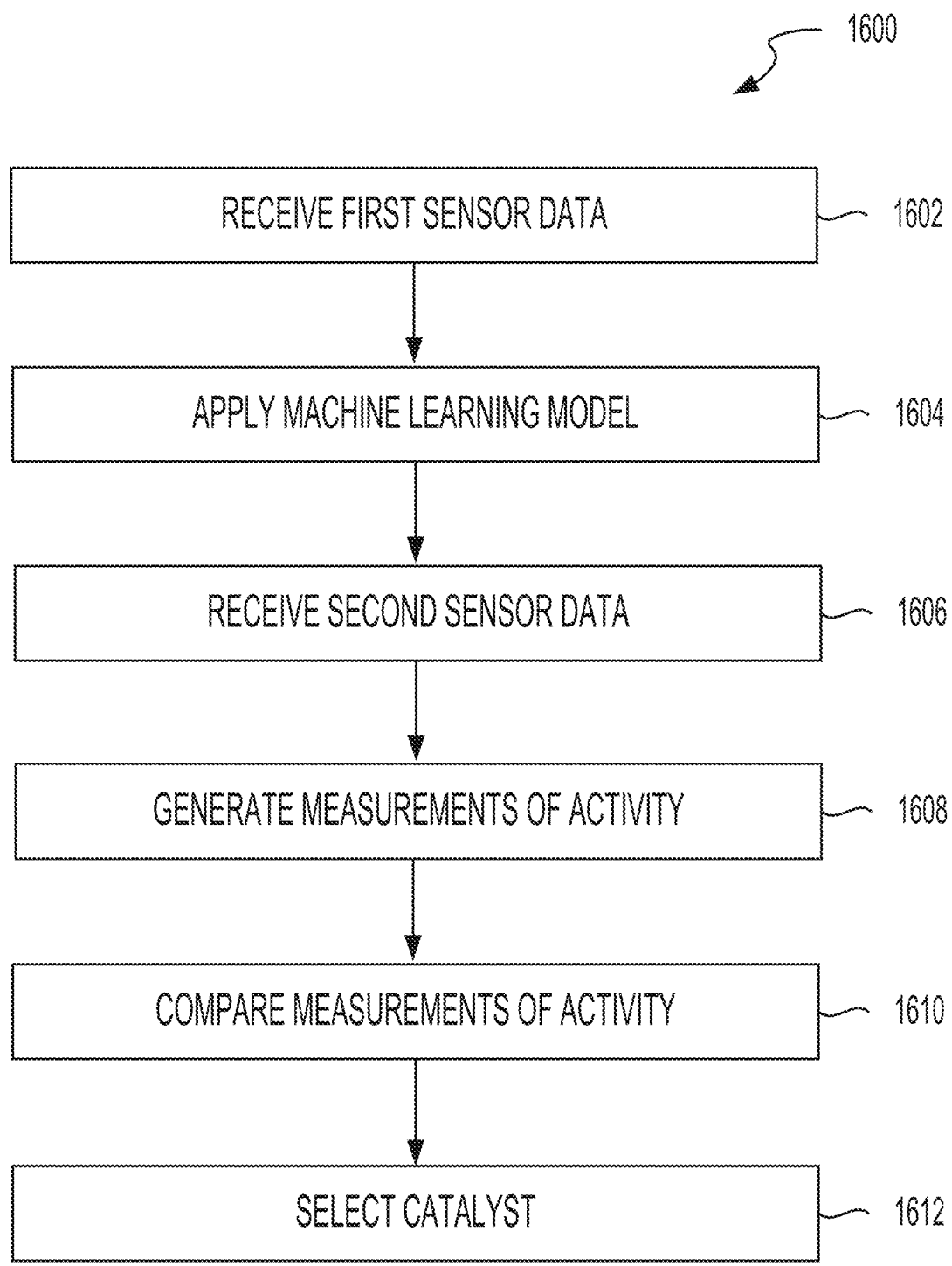
FIG. 16 illustrates a method of controlling parameters of a reactor, according to an example implementation.

FIG. 16 illustrates a method 1600 of controlling parameters of a reactor, according to an example implementation. The method 1600 can be implemented using various systems and devices described herein, such as the reactor platform 1302 and reactor system 1400. In brief summary, the method 1600 can include receiving first sensor data (BLOCK 1602). The method 1600 can include applying one or more machine learning models (BLOCK 1604). The method 1600 can include receiving second sensor data (BLOCK 1606). The method 1600 can include generating measurements of activity (BLOCK 1608). The method 1600 can include comparing measurements of activity (BLOCK 1610). The method 1600 can include selecting a catalyst (BLOCK 1612).

The method 1600 can include receiving first sensor data (BLOCK 1602). The method can include receiving, by processing circuitry, first sensor data. The first sensor data can include data regarding a reaction from one or more sensors that detect the first sensor data by monitoring a reactor. For example, the one or more sensors can include an infrared camera to capture thermal information of a reaction. The infrared camera can monitor thermal fluctuations of the reaction. The first sensor data can include molecular weight, polydispersity, or cross-linking. The first sensor data can include a temperature of the reaction or a flow rate of the reaction. The first sensor data can include dynamic light scattering data, nuclear magnetic resonance data or high performance liquid chromatography data. The dynamic light scattering data can be detected by a dynamic light scattering (DLS) sensor. The nuclear magnetic resonance data can be detected by a nuclear magnetic resonance (NMR) sensor. The high performance liquid chromatography data can be detected by a chromatography sensor.

The method 1600 can include applying one or more machine learning models (BLOCK 1604). The method can include applying one or more machine learning models to the first sensor data to generate a first measurement of activity of a first catalyst provided in the reactor. For example, the one or more machine learning models can include various models described herein, such as one or more ANNs trained to generate the measurement of activity of the catalysts based on sensor data such as temperature, flow rate, and concentration.

The method 1600 can include receiving second sensor data (BLOCK 1606). The method can include receiving, by processing circuitry, second sensor data. The second sensor data can include data regarding a second reaction of a second catalyst and at least one reactant. For example, the one or more sensors can include an infrared camera to capture thermal information of a reaction. The infrared camera can monitor thermal fluctuations of the reaction. The second sensor data can include molecular weight, polydispersity, or cross-linking. The second sensor data can include a temperature of the reaction or a flow rate of the reaction. The second sensor data can include dynamic light scattering data, nuclear magnetic resonance data or high performance liquid chromatography data. The dynamic light scattering data can be detected by a dynamic light scattering (DLS) sensor. The nuclear magnetic resonance data can be detected by a nuclear magnetic resonance (NMR) sensor. The high performance liquid chromatography data can be detected by a chromatography sensor.

The method 1600 can include generating measurements of activity (BLOCK 1608). The method can include generating, by the processing circuitry, a second measurement of activity of the second catalyst using the second sensor data. For example, the first measurement of activity can be greater than, less than, or equal to the second measurement of activity.

The method 1600 can include comparing measurements of activity (BLOCK 1610). The method can include comparing, by the processing circuitry, the second measurement of activity to the first measurement of activity. For example, the processing circuitry can compare the first measurement of activity to the second measurement of activity and determine that the first measurement of activity is greater than, less than, or equal to the second measurement of activity.

The method 1600 can include selecting a catalyst (BLOCK 1612). The method can include selecting, by the processing circuitry, one of the first catalyst or the second catalyst based on the comparison. For example, the processing circuitry can select the first catalyst based on the first measurement of activity being greater than the second measurement of activity.

Figure 17:
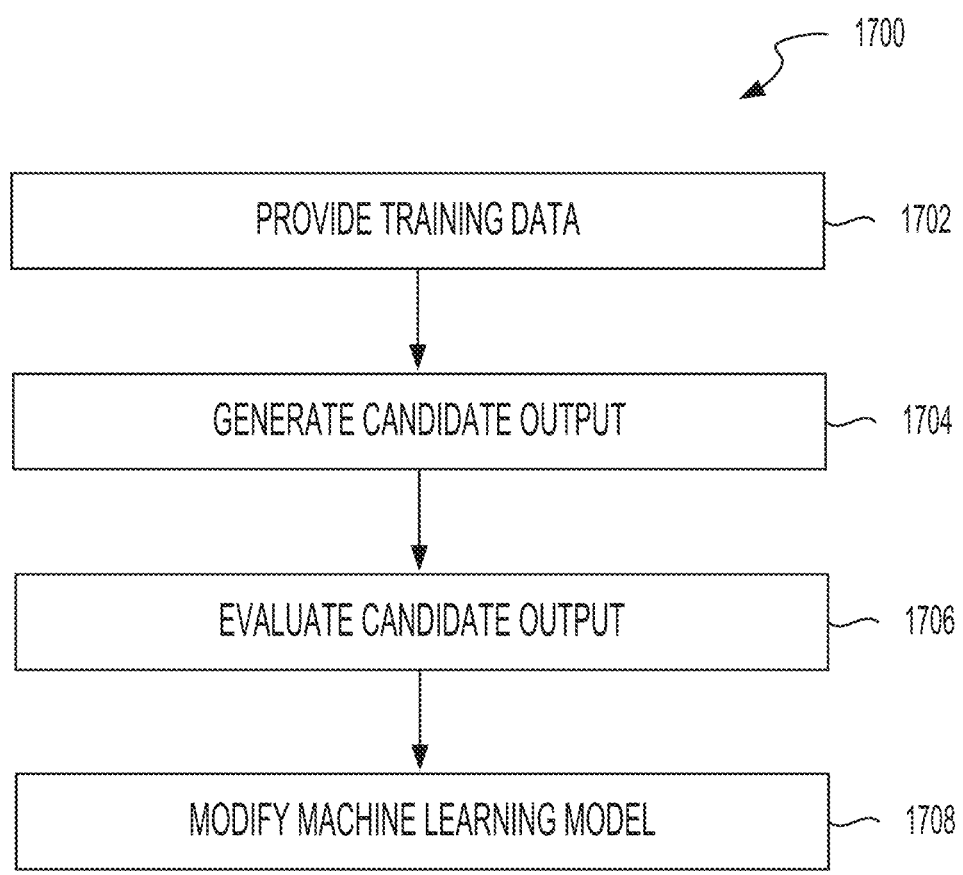
FIG. 17 illustrates a method of controlling parameters of a reactor, according to an example implementation.

FIG. 17 illustrates a method of controlling parameters of a reactor, according to an example implementation. The method 1700 can be implemented using various systems and devices described herein, such as the reactor platform 1302 and reactor system 1400. In brief summary, the method 1700 can include providing training data (BLOCK 1702). The method 1700 can include generating candidate output (BLOCK 1704). The method 1700 can include evaluating candidate output (BLOCK 1706). The method 1700 can include modifying the machine learning model (BLOCK 1708).

The method 1700 can include providing training data (BLOCK 1702). The method can include providing training data as input to a machine learning model. The training data can include a measure of catalytic activity of a reaction between at least one catalyst and at least one reactant. The training data can include at least one output parameter regarding at least one product generated by the reaction. The at least one output parameter can include at least one of a molecular weight or a polydispersity of the at least one product. The measure of catalytic activity can include at least one of a rate constant of the reaction, a lifetime of the at least one catalyst, or a turnover number of the at least one catalyst.

The method 1700 can include generating candidate output (BLOCK 1704). The method can include causing the machine learning model to generate candidate output responsive to the training data. The candidate output can include at least one candidate output parameter.

The method 1700 can include evaluating candidate output (BLOCK 1706). The method can include evaluating the candidate output using an objective function. Evaluating the candidate output can include comparing the at least one candidate output parameter to the at least one output parameter.

The method 1700 can include modifying the machine learning model (BLOCK 1708). The method can include modifying the machine learning model responsive to the evaluation. The method can include using the machine learning model as a digital twin. A digital twin can include a process whereby a mathematic model (e.g., ANN) is used in lieu of a physical system to draw potentially relevant conclusions. For example, the method can include modifying the machine model as a digital twin. The algorithm can run the machine learning model as a digital twin and use the results to find a probable maximum. The method can repeat or iterate until a probable maximum is found. The algorithm can include training the machine learning model based on results, finding the maximum productivity point, taking conditions at the maximum and assigning 0.5× and 2× concentrations as the maximum and minimum for Latin Hypercube trials, getting new conditions based on gradient, checking that new conditions are within reasonable norms, and assigning new conditions to the digital twin.

Embodiments of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The operations described in this specification can be performed by a data processing apparatus on data stored on one or more computer-readable storage devices or received from other sources. The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, subprograms, or portions of code). A computer program can be deployed to be executed on one computer or on multiple computers that are located at one site or distributed across multiple sites and interconnected by a communication network.

Processors suitable for the execution of a computer program include, by way of example, microprocessors, and any one or more processors of a digital computer. A processor can receive instructions and data from a read only memory or a random access memory or both. The elements of a computer are a processor for performing actions in accordance with instructions and one or more memory devices for storing instructions and data. A computer can include, or be operatively coupled to receive data from or transfer data to, or both, one or more mass storage devices for storing data, e.g., magnetic, magneto optical disks, or optical disks. A computer need not have such devices. Moreover, a computer can be embedded in another device, e.g., a personal digital assistant (PDA), a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The implementations described herein can be implemented in any of numerous ways including, for example, using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to or receive communications from other devices. The display unit(s) may be provided, for example, to allow a user to view various information in connection with execution of the instructions. The user input device(s) may be provided, for example, to allow the user to make manual adjustments, make selections, enter data or various other information, or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the solution discussed above. The computer readable medium or media can be transportable, such that the program or programs stored thereon can be loaded onto one or more different computers or other processors to implement various aspects of the present solution as discussed above.

The terms "program" or "software" are used herein to refer to any type of computer code or set of computer-executable instructions that can be employed to program a computer or other processor to implement various aspects of embodiments as discussed above. One or more computer programs that when executed perform methods of the present solution need not reside on a single computer or processor, but may be distributed in a modular fashion amongst a number of different computers or processors to implement various aspects of the present solution.

Computer-executable instructions may be in many forms, such as program modules, executed by one or more computers or other devices. Program modules can include routines, programs, objects, components, data structures, or other components that perform particular tasks or implement particular abstract data types. The functionality of the program modules can be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system, comprising:
    a flow reactor, comprising:
        at least one reactant provided to perform a reaction;
        one or more sensors configured to detect sensor data regarding the reaction; and
    processing circuitry configured to:
        receive the sensor data from the one or more sensors;
        apply one or more machine learning models to the sensor data to generate a measurement regarding at least one of kinetics of the reaction or an activity of at least one catalyst used to perform the reaction; and
        control at least one of a temperature of the flow reactor, a flow rate of the at least one reactant, or a concentration of the at least one reactant responsive to the measurement.

2. The system of claim 1, wherein the processing circuitry is configured to control the at least one of the temperature of the flow reactor, the flow rate of the at least one reactant, or the concentration of the at least one reactant to increase the measurement to be greater than a threshold measurement.

3. The system of claim 1, wherein the sensor data comprises at least one of molecular weight, polydispersity, cross-linking, temperature of the reaction, or flow rate of the reaction.

4. The system of claim 1, wherein the sensor data comprises at least one of dynamic light scattering data detected by a dynamic light scattering (DLS) sensor, nuclear magnetic resonance data detected by a nuclear magnetic resonance (NMR) sensor, high performance liquid chromatography data detected by a chromatography sensor, gel permeation chromatography (GPC) data detected by a chromatography sensor, calorimetry data detected by a calorimeter sensor, melting point data collected by a melting point sensor, viscometry data detected by a viscosity sensor, absorbance spectroscopy data detected by an infrared, visible, or ultraviolet sensor, X-ray scattering detected by an X-ray sensor, Raman spectroscopy data collected by a Raman spectroscopy sensor, cyclic voltammetry data collected by a potentiostat sensor, or millimeter wave data collected by a radio frequency sensor.

5. The system of claim 1, wherein the one or more sensors comprises an infrared sensor.

6. The system of claim 1, wherein the at least one reactant comprises a first reactant of a first phase and a second reactant of a second phase, the second phase different from the first phase.

7. The system of claim 1, wherein the at least one reactant comprises a polymer, and the reaction comprises a depolymerization reaction.

8. The system of claim 1, wherein the processing circuitry is configured to use the one or more machine learning models as a digital twin.

9. The system of claim 1, wherein the flow reactor, the one or more sensors, and the processing circuitry are portable.

10. The system of claim 1 wherein the flow reactor, the one or more sensors, and the processing circuitry are components of an autonomous system.

11. A method comprising:
receiving, by processing circuitry, sensor data regarding a reaction from one or more sensors that detect the sensor data by monitoring a flow reactor;
applying, by the processing circuitry, one or more machine learning models to the sensor data to generate a measurement regarding at least one of kinetics of the reaction or an activity of at least one catalyst provided in the flow reactor; and
controlling, by the processing circuitry, at least one of a temperature of the flow reactor, a flow rate of at least one reactant of the flow reactor, or a concentration of the at least one reactant responsive to the measurement.

12. The method of claim 11, wherein the processing circuitry is configured to control the at least one of the temperature of the flow reactor, the flow rate of the at least one reactant, or the concentration of the at least one reactant to increase the measurement to be greater than a threshold measurement.

13. The method of claim 11, wherein the sensor data comprises at least one of molecular weight, polydispersity, or cross-linking.

14. The method of claim 11, wherein the sensor data comprises at least one of a temperature of the reaction or a flow rate of the reaction.

15. The method of claim 11, wherein the sensor data comprises at least one of dynamic light scattering data detected by a dynamic light scattering (DLS) sensor, nuclear magnetic resonance data detected by a nuclear magnetic resonance (NMR) sensor, high performance liquid chromatography data detected by a chromatography sensor, gel permeation chromatography (GPC) data detected by a chromatography sensor, calorimetry data detected by a calorimeter sensor, melting point data collected by a melting point sensor, viscometry data detected by a viscosity sensor, absorbance spectroscopy data detected by an infrared, visible, or ultraviolet sensor, X-ray scattering detected by an X-ray sensor, Raman spectroscopy data collected by a Raman spectroscopy sensor, cyclic voltammetry data collected by a potentiostat sensor, or millimeter wave data collected by a radio frequency sensor.

16. A method, comprising:
providing training data as input to a machine learning model, the training data comprising (1) a measure of catalytic activity of a reaction between at least one catalyst and at least one reactant and (2) at least one output parameter regarding at least one product generated by the reaction;
causing the machine learning model to generate candidate output responsive to the training data, the candidate output comprising at least one candidate output parameter;
evaluating the candidate output using an objective function;
modifying the machine learning model responsive to the evaluation.

17. The method of claim 16, wherein the at least one output parameter includes at least one of a molecular weight or a polydispersity of the at least one product.

18. The method of claim 16, wherein evaluating the candidate output includes comparing the at least one candidate output parameter to the at least one output parameter.

19. The method of claim 16, wherein the measure of catalytic activity includes at least one of a rate constant of the reaction, a lifetime of the at least one catalyst, or a turnover number of the at least one catalyst.

20. The method of claim 16, comprising:
using the machine learning model as a digital twin.

* * * * *

UNITED STATES PATENT AND TRADEMARK OFFICE
CERTIFICATE OF CORRECTION

PATENT NO. : 11,992,818 B2
APPLICATION NO. : 16/999842
DATED : May 28, 2024
INVENTOR(S) : Ryan Lee Hartman and Benjamin A. Rizkin It is certified that error appears in the above-identified patent and that said Letters Patent is hereby corrected as shown below:

In the Specification

Column 1, Line 12, following after the "Cross Reference to Related Applications" add new sub-heading and paragraph:
STATEMENT OF GOVERNMENT INTEREST
"This invention was made with government support under 1701393 awarded by the National Science Foundation to New York University. The government has certain rights in the invention."

Signed and Sealed this
Third Day of September, 2024

Katherine Kelly Vidal
*Director of the United States Patent and Trademark Office*